(12) United States Patent
Villarta et al.

(10) Patent No.: US 9,839,787 B2
(45) Date of Patent: Dec. 12, 2017

(54) SYSTEMS AND METHODS FOR MAKING AND USING CONNECTOR CONTACT ARRAYS FOR ELECTRICAL STIMULATION SYSTEMS

(71) Applicant: Boston Scientific Neuromodulation Corporation, Valencia, CA (US)

(72) Inventors: Geoffrey Abellana Villarta, Castaic, CA (US); Joshua Dale Howard, Sacramento, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/490,656

(22) Filed: Apr. 18, 2017

(65) Prior Publication Data

US 2017/0216604 A1    Aug. 3, 2017

Related U.S. Application Data

(62) Division of application No. 15/208,515, filed on Jul. 12, 2016, now Pat. No. 9,656,093.
(Continued)

(51) Int. Cl.
*A61N 1/375*    (2006.01)
*A61N 1/05*    (2006.01)

(52) U.S. Cl.
CPC ............. *A61N 1/3752* (2013.01); *A61N 1/05* (2013.01)

(58) Field of Classification Search
CPC .......... A61N 1/3752; A61N 1/05; A61N 1/36; A61N 1/372
(Continued)

(56) References Cited

U.S. PATENT DOCUMENTS 4,602,624 A    7/1986    Naples et al.
4,630,611 A    12/1986    King
(Continued)

FOREIGN PATENT DOCUMENTS

EP    0580928 A1    2/1994
EP    0650694 B1    7/1998
(Continued)

OTHER PUBLICATIONS

International Search Report and Written Opinion for PCT/US2016/041938 dated Oct. 14, 2016, 14 pages.
(Continued)

*Primary Examiner* — Alexander Gilman
(74) *Attorney, Agent, or Firm* — Lowe Graham Jones PLLC; Bruce E. Black

(57) ABSTRACT

A connector for an implantable electrical medical device includes an elongated connector body; a connector lumen to receive a lead or lead extension; a non-conductive carrier disposed in the connector body and including at least two rails extending parallel to the connector lumen and pairs of contact holders spaced-apart along the rails; contacts with each contact disposed between one of the pairs of contact holders; and connector conductors coupled to the contacts. Instead of carrier and contacts, the connector can include contact assemblies, each contact assembly including a non-conductive contact carrier defining two nodes, and two contacts, each contact disposed in one of the two nodes, each contact including a coil and a sheath disposed around at least a portion of the coil. Another alternative includes a non-conductive carrier with contact openings; and contacts, where each contact is a rod disposed in one of the contact openings.

20 Claims, 13 Drawing Sheets

Related U.S. Application Data

(60) Provisional application No. 62/193,472, filed on Jul. 16, 2015.

(58) Field of Classification Search
USPC .................................. 439/600; 607/116, 37
See application file for complete search history.

(56) References Cited

U.S. PATENT DOCUMENTS

| | | | |
|---|---|---|---|
| 4,744,370 A | 5/1988 | Harris | |
| 5,000,194 A | 3/1991 | van den Honert et al. | |
| 5,070,605 A | 12/1991 | Daglow et al. | |
| 5,135,001 A | 8/1992 | Sinofsky et al. | |
| 5,348,481 A * | 9/1994 | Ortiz | H01R 24/58 439/25 |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,843,148 A | 12/1998 | Gijsbers et al. | |
| 5,938,688 A | 8/1999 | Schiff | |
| 5,987,361 A | 11/1999 | Mortimer | |
| 6,018,684 A | 1/2000 | Bartig et al. | |
| 6,125,302 A | 9/2000 | Kuzma | |
| 6,134,478 A | 10/2000 | Spehr | |
| 6,161,047 A | 12/2000 | King et al. | |
| 6,162,101 A * | 12/2000 | Fischer | A61B 5/0422 439/729 |
| 6,167,311 A | 12/2000 | Rezai | |
| 6,181,969 B1 | 1/2001 | Gord | |
| 6,322,559 B1 | 11/2001 | Daulton et al. | |
| 6,428,336 B1 * | 8/2002 | Akerfeldt | H01R 12/63 439/263 |
| 6,510,347 B2 | 1/2003 | Borkan | |
| 6,516,227 B1 | 2/2003 | Meadows et al. | |
| 6,556,873 B1 | 4/2003 | Smits | |
| 6,564,078 B1 | 5/2003 | Marino et al. | |
| 6,609,029 B1 | 8/2003 | Mann et al. | |
| 6,609,032 B1 | 8/2003 | Woods et al. | |
| 6,663,570 B2 * | 12/2003 | Mott | A61B 5/0215 439/909 |
| 6,678,564 B2 | 1/2004 | Ketterl et al. | |
| 6,741,892 B1 * | 5/2004 | Meadows | A61N 1/3752 607/116 |
| 6,757,970 B1 | 7/2004 | Kuzma et al. | |
| 7,027,852 B2 | 4/2006 | Helland | |
| 7,047,084 B2 | 5/2006 | Erickson et al. | |
| 7,108,549 B2 * | 9/2006 | Lyu | H01R 13/5224 439/587 |
| 7,203,548 B2 | 4/2007 | Whitehurst et al. | |
| 7,241,180 B1 | 7/2007 | Rentas | |
| 7,244,150 B1 * | 7/2007 | Brase | A61N 1/0551 439/668 |
| 7,292,890 B2 | 11/2007 | Whitehurst et al. | |
| 7,402,083 B2 * | 7/2008 | Kast | A61N 1/3752 439/660 |
| 7,437,193 B2 | 10/2008 | Parramon et al. | |
| 7,450,997 B1 | 11/2008 | Pianca et al. | |
| 7,489,971 B1 | 2/2009 | Franz | |
| 7,668,601 B2 | 2/2010 | Hegland et al. | |
| 7,672,734 B2 | 3/2010 | Anderson et al. | |
| 7,736,191 B1 * | 6/2010 | Sochor | A61N 1/3752 439/668 |
| 7,761,165 B1 | 7/2010 | He et al. | |
| 7,761,985 B2 | 7/2010 | Hegland et al. | |
| 7,783,359 B2 | 8/2010 | Meadows | |
| 7,792,590 B1 | 9/2010 | Pianca et al. | |
| 7,798,864 B2 * | 9/2010 | Barker | A61N 1/3752 439/668 |
| 7,809,446 B2 | 10/2010 | Meadows | |
| 7,822,482 B2 | 10/2010 | Gerber | |
| 7,840,188 B2 | 11/2010 | Kurokawa | |
| 7,848,802 B2 | 12/2010 | Goetz | |
| 7,856,707 B2 | 12/2010 | Cole | |
| 7,860,570 B2 | 12/2010 | Whitehurst et al. | |
| 7,949,395 B2 | 5/2011 | Kuzma | |
| 7,974,705 B2 | 7/2011 | Zdeblick et al. | |
| 7,974,706 B2 | 7/2011 | Moffitt et al. | |
| 7,979,140 B2 | 7/2011 | Schulman | |
| 8,000,808 B2 | 8/2011 | Hegland et al. | |
| 8,019,440 B2 | 9/2011 | Kokones et al. | |
| 8,036,755 B2 | 10/2011 | Franz | |
| 8,041,309 B2 | 10/2011 | Kurokawa | |
| 8,046,074 B2 * | 10/2011 | Barker | A61N 1/05 607/37 |
| 8,099,177 B2 | 1/2012 | Dahlberg | |
| 8,100,726 B2 * | 1/2012 | Harlan | H01R 13/2414 29/883 |
| 8,140,163 B1 * | 3/2012 | Daglow | A61N 1/3752 607/36 |
| 8,175,710 B2 | 5/2012 | He | |
| 8,190,259 B1 * | 5/2012 | Smith | A61N 1/3752 607/36 |
| 8,224,450 B2 | 7/2012 | Brase | |
| 8,225,504 B2 | 7/2012 | Dye et al. | |
| 8,239,042 B2 * | 8/2012 | Chinn | A61N 1/3752 600/372 |
| 8,271,094 B1 | 9/2012 | Moffitt et al. | |
| 8,295,944 B2 | 10/2012 | Howard et al. | |
| 8,301,255 B2 * | 10/2012 | Barker | A61N 1/3752 604/538 |
| 8,321,025 B2 | 11/2012 | Bedenbaugh | |
| 8,342,887 B2 * | 1/2013 | Gleason | A61B 1/00124 439/668 |
| 8,359,107 B2 | 1/2013 | Pianca et al. | |
| 8,364,278 B2 | 1/2013 | Pianca et al. | |
| 8,391,985 B2 | 3/2013 | McDonald | |
| 8,583,237 B2 | 11/2013 | Bedenbaugh | |
| 8,688,235 B1 | 4/2014 | Pianca et al. | |
| 8,849,415 B2 * | 9/2014 | Bedenbaugh | H01R 4/363 607/115 |
| 8,897,891 B2 * | 11/2014 | Romero | A61N 1/0556 607/116 |
| 8,968,331 B1 * | 3/2015 | Sochor | A61N 1/0534 606/129 |
| 9,101,775 B2 * | 8/2015 | Barker | A61N 1/3752 |
| 9,149,630 B2 * | 10/2015 | Howard | A61N 1/0534 |
| 9,162,048 B2 * | 10/2015 | Romero | A61N 1/0529 |
| 9,270,070 B2 * | 2/2016 | Pianca | A61N 1/05 |
| 9,289,596 B2 * | 3/2016 | Leven | A61N 1/05 |
| 9,352,147 B2 * | 5/2016 | Nguyen-Stella | A61N 1/0558 |
| 9,381,348 B2 * | 7/2016 | Romero | A61N 1/0551 |
| 9,403,022 B2 * | 8/2016 | Ries | A61N 1/375 |
| 9,409,032 B2 * | 8/2016 | Brase | A61N 1/3752 |
| 9,440,066 B2 * | 9/2016 | Black | A61N 1/3752 |
| 9,498,620 B2 * | 11/2016 | Romero | A61N 1/0534 |
| 9,504,839 B2 * | 11/2016 | Leven | A61N 1/0553 |
| 2001/0023368 A1 | 9/2001 | Black et al. | |
| 2002/0156513 A1 | 10/2002 | Borkan | |
| 2002/0183817 A1 | 12/2002 | Van Venrooij et al. | |
| 2005/0015130 A1 | 1/2005 | Gill | |
| 2005/0038489 A1 | 2/2005 | Grill | |
| 2005/0171587 A1 | 8/2005 | Daglow et al. | |
| 2006/0025841 A1 | 2/2006 | McIntyre | |
| 2006/0247697 A1 | 11/2006 | Sharma et al. | |
| 2007/0150036 A1 | 6/2007 | Anderson | |
| 2007/0168007 A1 | 7/2007 | Kuzma et al. | |
| 2007/0203546 A1 | 8/2007 | Stone et al. | |
| 2007/0219551 A1 | 9/2007 | Honour et al. | |
| 2008/0077186 A1 | 3/2008 | Thompson et al. | |
| 2008/0103580 A1 | 5/2008 | Gerber | |
| 2008/0114230 A1 | 5/2008 | Addis | |
| 2008/0215125 A1 | 9/2008 | Farah et al. | |
| 2008/0255647 A1 | 10/2008 | Jensen et al. | |
| 2009/0054941 A1 * | 2/2009 | Eggen | A61N 1/0565 607/9 |
| 2009/0187222 A1 | 7/2009 | Barker | |
| 2009/0204192 A1 | 8/2009 | Carlton et al. | |
| 2009/0276021 A1 | 11/2009 | Meadows et al. | |
| 2010/0030298 A1 | 2/2010 | Martens et al. | |

(56) References Cited

U.S. PATENT DOCUMENTS

| | | |
|---|---|---|
| 2010/0036468 A1 | 2/2010 | Decre et al. |
| 2010/0057176 A1 | 3/2010 | Barker |
| 2010/0070012 A1* | 3/2010 | Chinn ................. A61N 1/0553 607/152 |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1* | 6/2011 | Chen ................. A61N 1/0534 607/116 |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071937 A1* | 3/2012 | Sundaramurthy ... A61N 1/3752 607/2 |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203302 A1* | 8/2012 | Moffitt ................. A61N 1/0529 607/45 |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1* | 9/2012 | Sage ................. A61N 1/3752 607/2 |
| 2012/0259386 A1 | 10/2012 | DeRohan et al. |
| 2012/0316615 A1* | 12/2012 | DiGiore ............. A61N 1/0534 607/45 |
| 2013/0105071 A1 | 5/2013 | DiGiore et al. |
| 2013/0109254 A1* | 5/2013 | Klardie ............. A61N 1/0534 439/887 |
| 2013/0197424 A1 | 8/2013 | Bedenbaugh |
| 2013/0197602 A1 | 8/2013 | Pianca et al. |
| 2013/0197603 A1* | 8/2013 | Eiger ................. H01R 13/02 607/46 |
| 2013/0261684 A1 | 10/2013 | Howard |
| 2013/0288501 A1* | 10/2013 | Russell ............. H01R 13/648 439/271 |
| 2013/0304140 A1* | 11/2013 | DeRohan ............. A61N 1/05 607/2 |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0151113 A1 | 6/2015 | Govea et al. |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1* | 5/2016 | Malinowski ......... A61N 1/0551 607/116 |
| 2016/0129265 A1 | 5/2016 | Malinowski |
| 2016/0228692 A1 | 8/2016 | Steinke et al. |
| 2016/0296745 A1 | 10/2016 | Govea et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

OTHER PUBLICATIONS

U.S. Appl. No. 62/193,472, Entitled: Systems and Methods for Making and Using Connector Contact Arrays for Electrical Stimulation Leads, Inventor: Villarta et al., filed Jul. 16, 2015, 52 pages.

U.S. Appl. No. 15/208,515, Entitled: Systems and Methods for Making and Using Connector Contact Arrays for Electrical Stimulation Leads, Inventor: Villarta et al., filed Jul. 12, 2016, 49 pages.

* cited by examiner

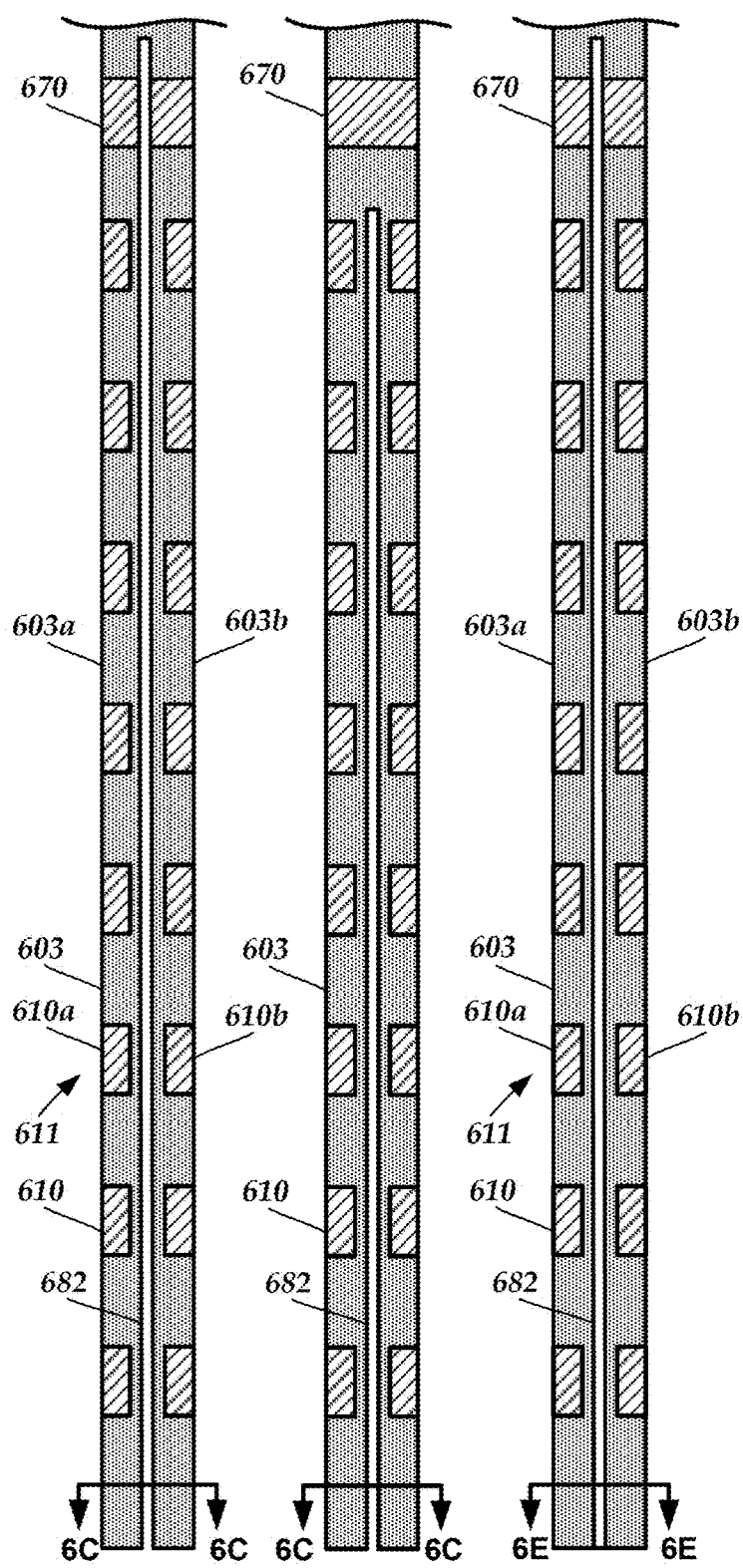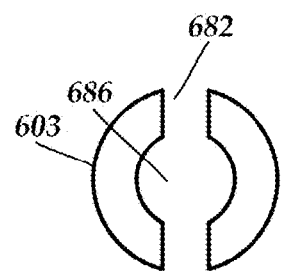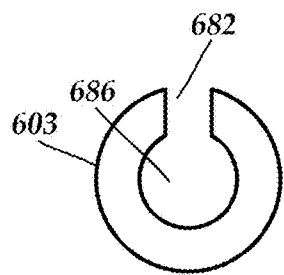
Fig. 6A  Fig. 6B  Fig. 6D
Fig. 6C
Fig. 6E

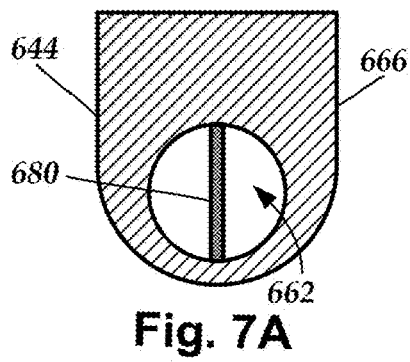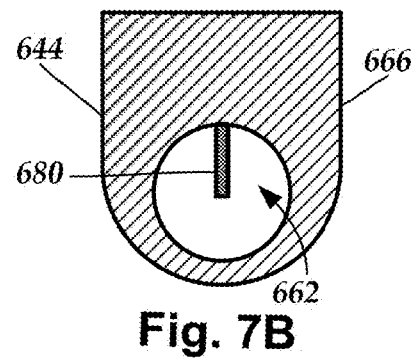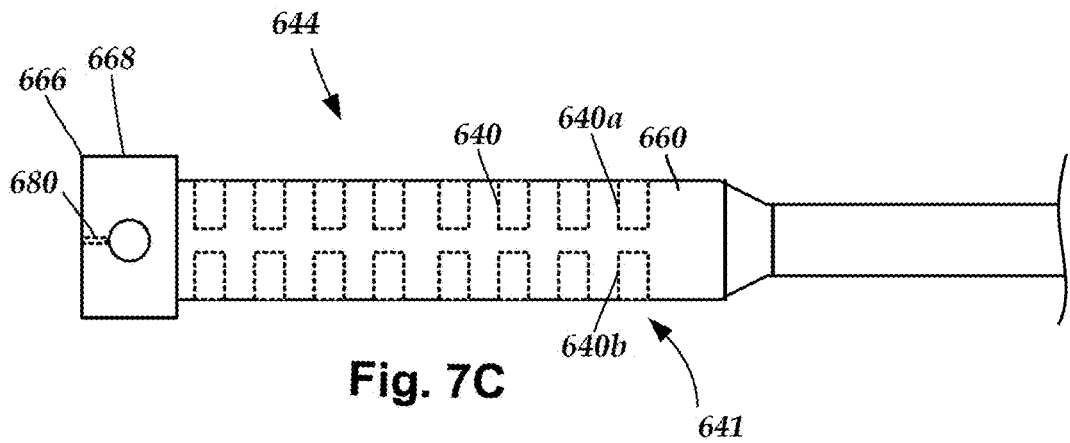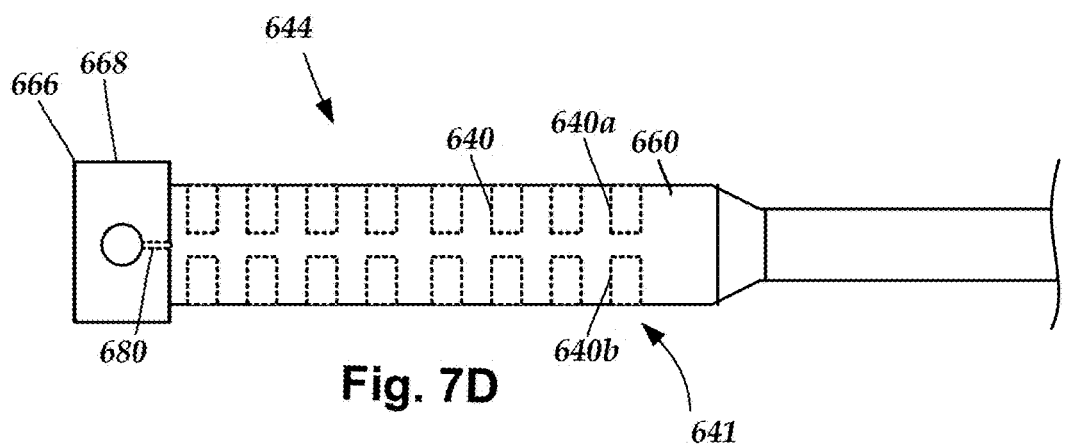

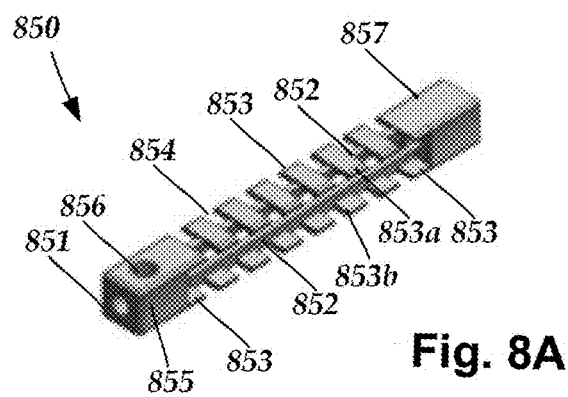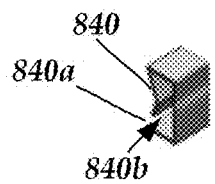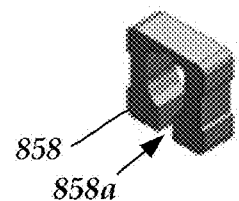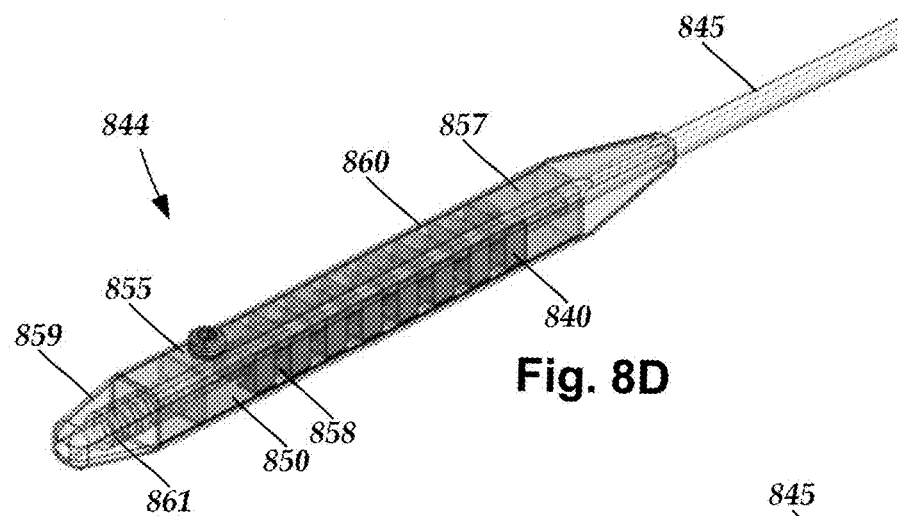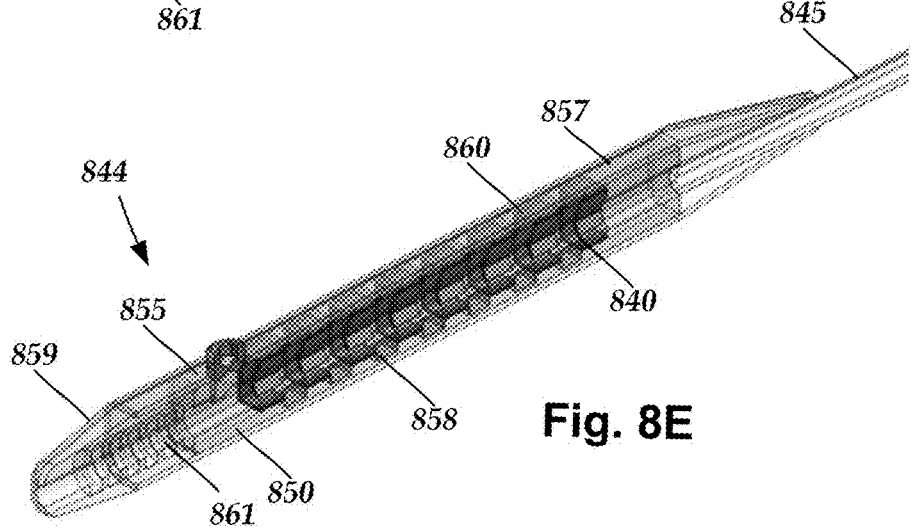

SYSTEMS AND METHODS FOR MAKING AND USING CONNECTOR CONTACT ARRAYS FOR ELECTRICAL STIMULATION SYSTEMS

CROSS-REFERENCE TO RELATED APPLICATIONS

This application is a divisional of U.S. patent application Ser. No. 15/208,515 filed Jul. 12, 2016 which claims the benefit under 35 U.S.C. §119(e) of U.S. Provisional Patent Application Ser. No. 62/193,472, filed Jul. 16, 2015, both of which are incorporated herein by reference.

FIELD

The present invention is directed to the area of implantable electrical stimulation systems and methods of making and using the systems. The present invention is also directed to implantable electrical stimulation systems having connector contact arrays for receiving split proximal contact arrays, as well as methods of making and using the elongated devices, contact arrays, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a connector for an implantable electrical medical device that includes an elongated connector body having a first end and an opposing second end; a connector lumen defined in the connector body to receive a lead or lead extension; a non-conductive carrier disposed in the connector body and including at least two rails extending parallel to the connector lumen and a plurality of pairs of contact holders spaced-apart along the rails, where each pair of contact holders includes two opposing contact holders; contacts with each contact disposed between one of the pairs of contact holders; and connector conductors coupled to the contacts.

In at least some embodiments, the carrier further includes a retainer element coupled to the at least two rails. In at least some embodiments, the carrier further includes a stop element coupled to the at least two rails opposite the retainer element. In at least some embodiments, one of the pair of contact holders is coupled to either the retainer element or the stop element.

In at least some embodiments, the carrier defines openings between adjacent pairs of contact holders, the connector further including a non-conductive spacer disposed in each of the openings. In at least some embodiments, the connector further includes a tapered snout coupled to the first end of the connector body. In at least some embodiments, the tapered snout defines a lumen extending to the connector lumen and ridged features disposed within the lumen to form a seal when the lead or lead extension is received by the connector lumen.

Another embodiment is a connector for an implantable electrical medical device that includes an elongated connector body having a first end and an opposing second end; a connector lumen defined in the connector body and configured and arranged to receive a lead or lead extension; and contact assemblies disposed in the connector lumen. Each contact assembly includes a non-conductive contact carrier defining a lumen with two nodes, and two contacts, each contact disposed in one of the two nodes such that the two contacts are not in electrical contact with one another, each contact including a coil and a sheath disposed around at least a portion of the coil. The connector also includes connector conductors electrically coupled to the contact assemblies.

In at least some embodiments, a longitudinal axis of the coil of each contact is parallel to the connector lumen. In at least some embodiments, the sheath extends around at least 50% of a circumference of the coil. In at least some embodiments, the connector conductors are attached to the sheaths of the contacts of the contact assemblies. In at least some embodiments, the two nodes of each contact carrier are disposed opposite each other. In at least some embodiments, the two nodes of all of the contact carriers are aligned along the connector lumen. In at least some embodiments, the connector further includes a retainer element, an end stop element, or both disposed in the connector body.

Yet another embodiment is a connector for an implantable electrical medical device that includes an elongated connector body having a first end and an opposing second end; a connector lumen defined in the connector body and configured and arranged to receive a lead or lead extension; a non-conductive carrier disposed in the connector body and including contact openings spaced apart from each other, contacts where each contact is a rod disposed in one of the contact openings of the carrier; and of connector conductors coupled to the contacts.

In at least some embodiments, the contacts are aligned perpendicular the connector lumen. In at least some embodiments, the contact openings form pairs of contact openings disposed opposite each other with respect to the connector lumen. In at least some embodiments, the contact openings forms two rows of contact openings with one of the rows of contact openings offset from another of the rows of contact openings. In at least some embodiments, the carrier is formed of a springy material that is compressed by the contacts when the lead or lead extension is received in the connector lumen. In at least some embodiments, the connector further includes a retainer element, an end stop element, or both disposed in the connector body.

A further embodiment is a lead extension including a lead extension body with a proximal portion, a distal portion, a circumference, and a longitudinal length; any one of the connectors described above disposed along the distal portion of the lead extension body; and lead extension terminals disposed along the proximal portion of the lead extension body. The connector conductors electrically couple the contacts of the connector to the lead extension terminals.

Another embodiments is a control module including a sealed housing; an electronic subassembly disposed in the sealed housing; a header coupled to the sealed housing; and any one of the connectors described above disposed in the header.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 6A is a schematic side view of one embodiment of a proximal end of a lead containing segmented terminals and an alignment slit, according to the invention;

FIG. 6B is a schematic side view of a second embodiment of a proximal end of a lead containing segmented terminals and an alignment slit, according to the invention;

FIG. 6C is a schematic cross-sectional view of any one of the leads of FIGS. 6A-6B, according to the invention;

FIG. 6D is a schematic side view of a third embodiment of a proximal end of a lead containing segmented terminals and an alignment slit, according to the invention;

FIG. 6E is a schematic cross-sectional view of the lead of FIG. 6D, according to the invention;

FIG. 7A is schematic end view of one embodiment of a connector for receiving a lead containing segmented terminals, according to the invention;

FIG. 7B is schematic end view of a second embodiment of a connector for receiving a lead containing segmented terminals, according to the invention;

FIG. 7C is schematic side view of one embodiment of a connector for receiving a lead containing segmented terminals, according to the invention;

FIG. 7D is schematic side view of a second embodiment of a connector for receiving a lead containing segmented terminals, according to the invention;

FIG. 8A is a schematic perspective view of one embodiment of a carrier for a connector, according to the invention;

FIG. 8B is a schematic perspective view of one embodiment of a contact for a connector, according to the invention;

FIG. 8C is a schematic perspective view of one embodiment of a spacer for a connector, according to the invention;

FIG. 8D is a schematic perspective view of one embodiment of a connector incorporating the elements of FIGS. 8A-8C, according to the invention;

FIG. 8E is a schematic perspective cut-away view of the connector of FIG. 8D, according to the invention;

DETAILED DESCRIPTION

The present invention is directed to the area of implantable electrical stimulation systems and methods of making and using the systems. The present invention is also directed to implantable electrical stimulation systems having connector contact arrays for receiving split proximal contact arrays, as well as methods of making and using the elongated devices, contact arrays, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entirety.

Figure 1:
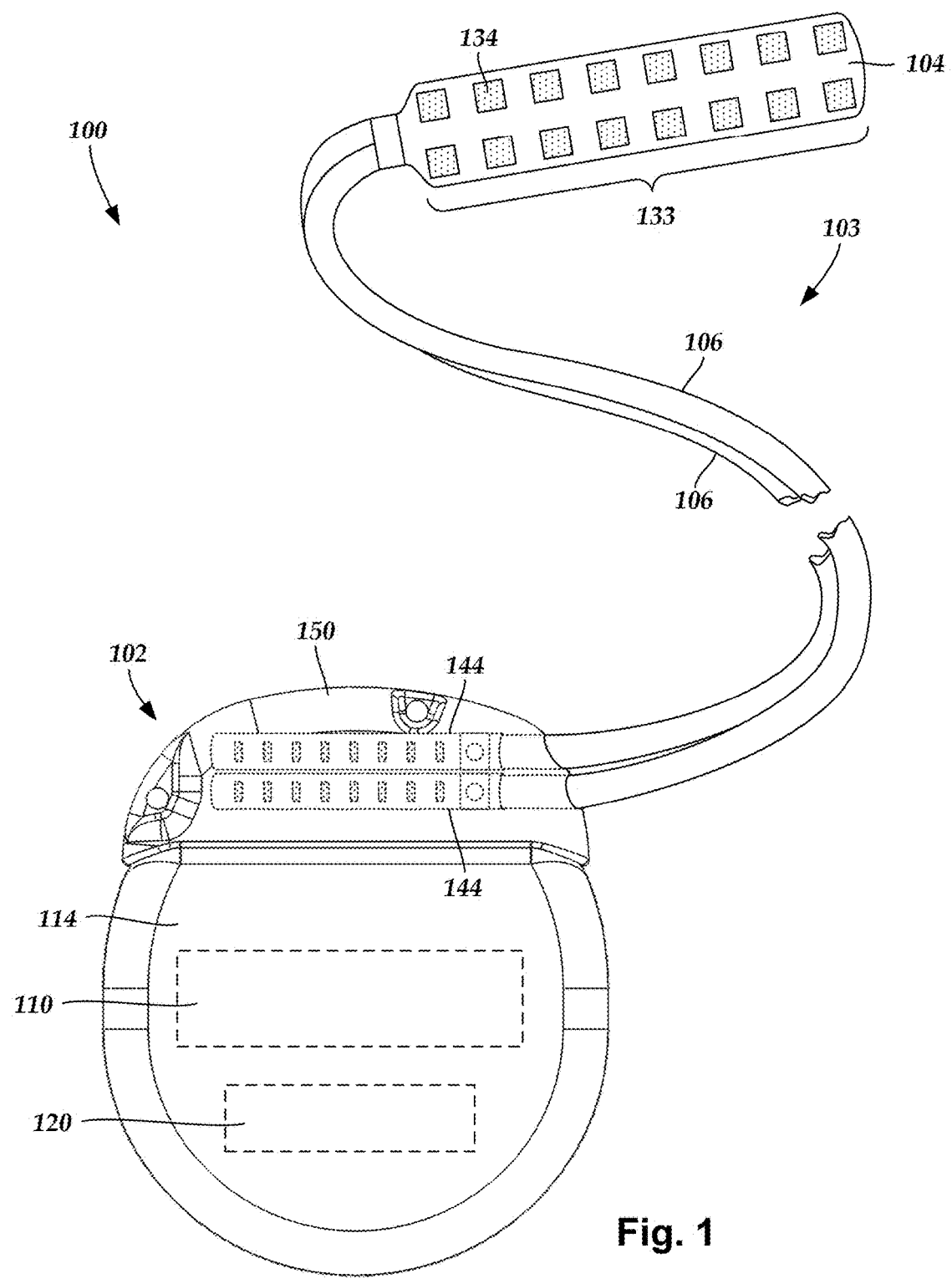
FIG. 1 is a schematic view of one embodiment of an implantable medical device that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connectors 144 into which the proximal end of the one or more lead bodies 106 can be plugged to make an electrical connection via connector contacts (e.g., 316 in FIG. 3A) disposed in the connector 144 and terminals (e.g., 310 in FIG. 3A) on each of the one or more lead bodies 106. The connector contacts are coupled to the electronic subassembly 110 and the terminals are coupled to the electrodes 134. In FIG. 1, two connectors 144 are shown.

The one or more connectors 144 may be disposed in a header 150. The header 150 provides a protective covering over the one or more connectors 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
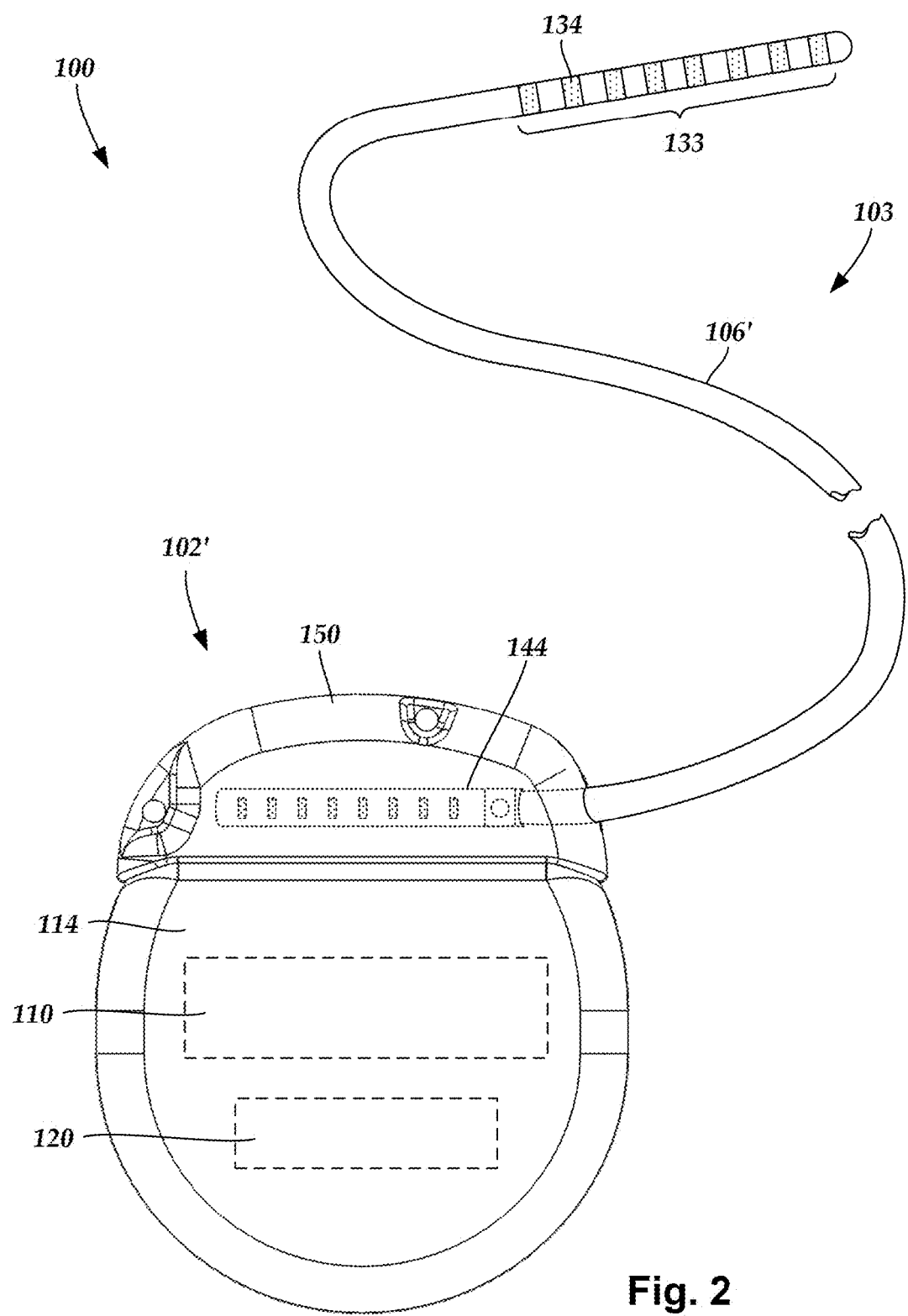
FIG. 2 is a schematic view of another embodiment of an implantable medical device that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connectors (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connectors 144 disposed on the control module 102. The control module 102 can include any suitable number of connectors 144 including, for example, two three, four, five, six, seven, eight, or more connectors 144. It will be understood that other numbers of connectors 144 may be used instead. In FIG. 1, each of the two lead bodies 106 includes eight terminals that are shown coupled with eight conductive contacts disposed in a different one of two different connectors 144.

Figure 3A:
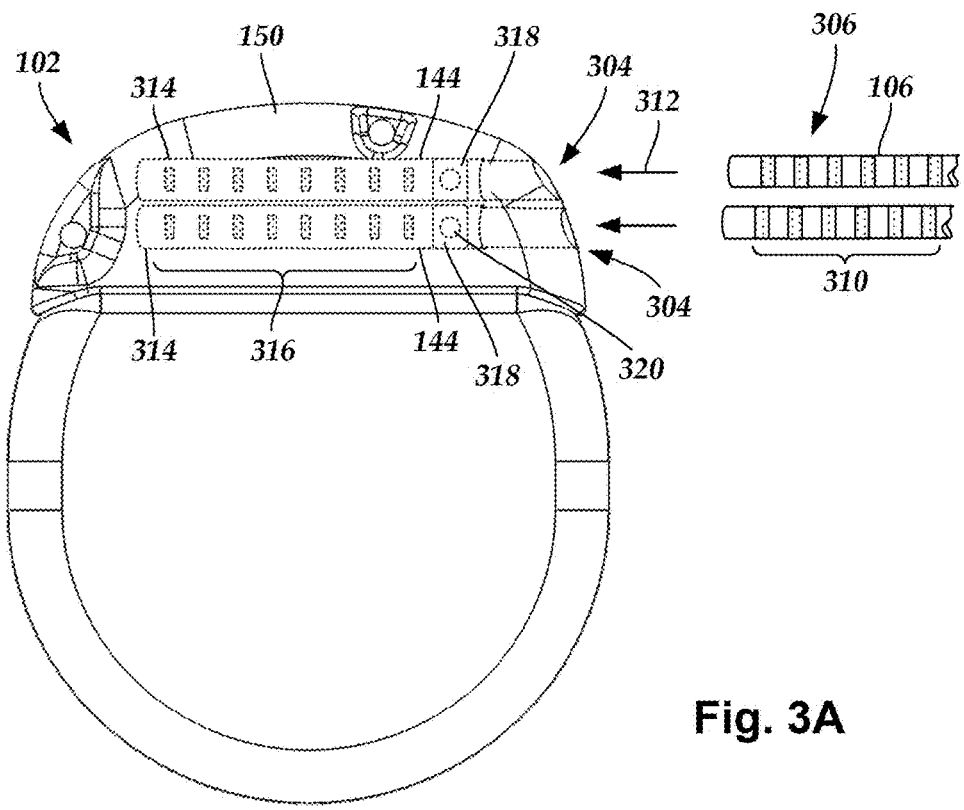
FIG. 3A is a schematic view of one embodiment of a plurality of connectors disposed in the control module of FIG. 1, the connectors configured and arranged to receive the proximal portions of the lead bodies of FIG. 1, according to the invention.
Figure 3B:
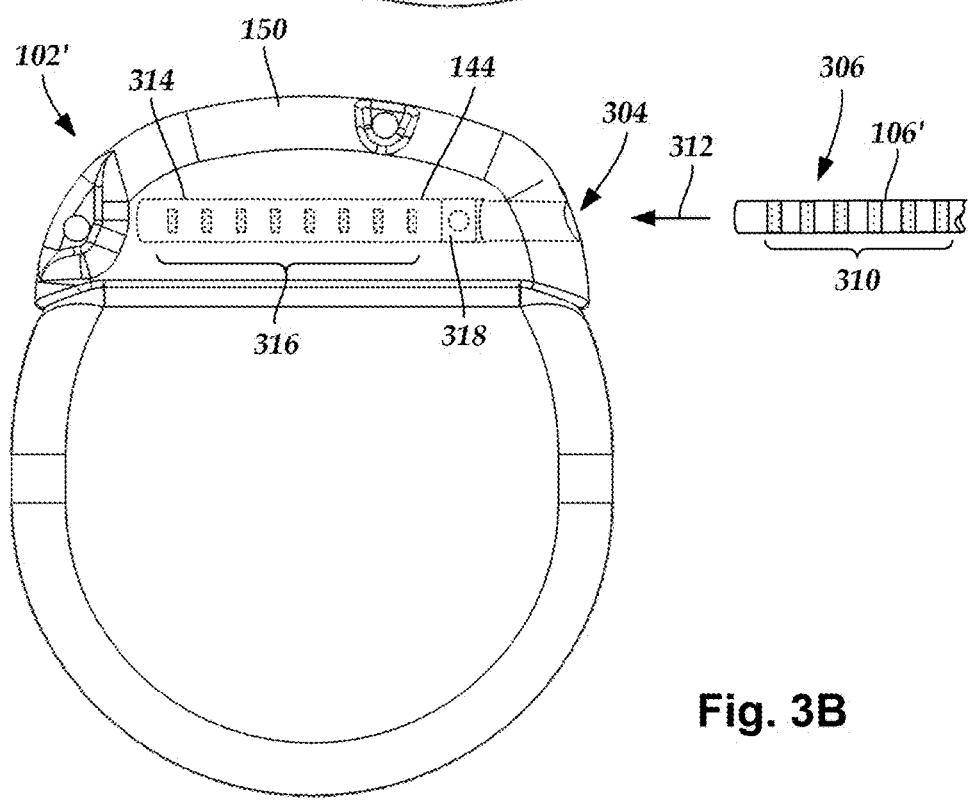
FIG. 3B is a schematic view of one embodiment of a connector disposed in the control module of FIG. 2, the connector configured and arranged to receive the proximal portion of one of the lead body of FIG. 2, according to the invention.

FIG. 3A is a schematic side view of one embodiment of a plurality of connectors 144 disposed on the control module 102. In at least some embodiments, the control module 102 includes two connectors 144. In at least some embodiments, the control module 102 includes four connectors 144. In FIG. 3A, proximal ends 306 of the plurality of lead bodies 106 are shown configured and arranged for insertion to the control module 102. FIG. 3B is a schematic side view of one embodiment of a single connector 144 disposed on the control module 102'. In FIG. 3B, the proximal end 306 of the single lead body 106' is shown configured and arranged for insertion to the control module 102'.

In FIGS. 3A and 3B, the one or more connectors 144 are disposed in the header 150. In at least some embodiments, the header 150 defines one or more lumens 304 into which the proximal end(s) 306 of the one or more lead bodies 106/106' with terminals 310 can be inserted, as shown by directional arrows 312, in order to gain access to the connector contacts disposed in the one or more connectors 144.

The one or more connectors 144 each include a connector housing 314 and a plurality of connector contacts 316 disposed therein. Typically, the connector housing 314 provides access to the plurality of connector contacts 316 via the lumen 304. In at least some embodiments, one or more of the connectors 144 further includes a retaining element 318 configured and arranged to fasten the corresponding lead body 106/106' to the connector 144 when the lead body 106/106' is inserted into the connector 144 to prevent undesired detachment of the lead body 106/106' from the connector 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more lumens 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connectors in control modules are found in, for example, U.S. Pat. Nos. 7,244,150 and 6,224,450, which are incorporated by reference in their entirety.

Figure 3C:
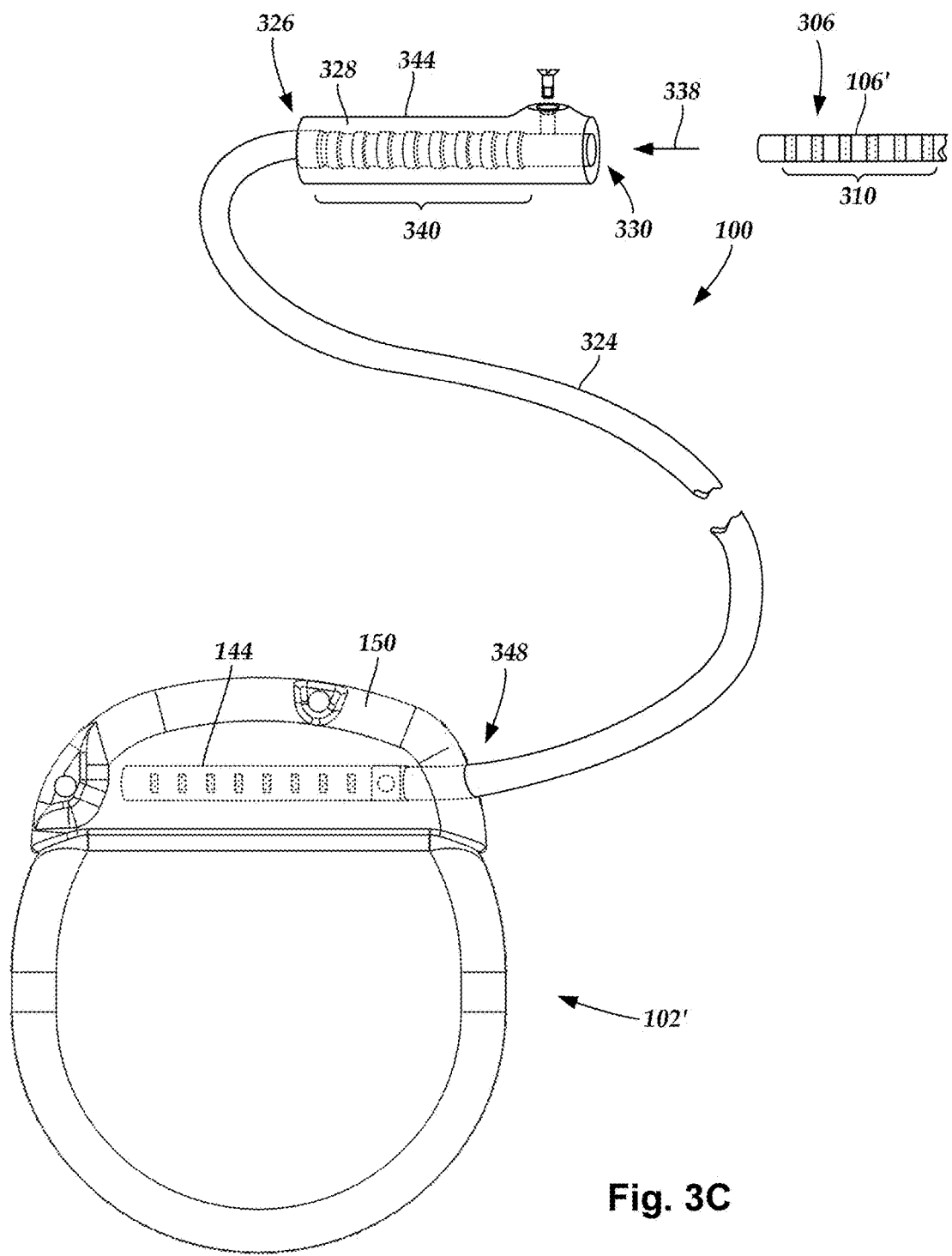
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector 322 is disposed on a lead extension 324. The lead extension connector 322 is shown disposed at a distal end 326 of the lead extension 324. The lead extension connector 322 includes a connector housing 344. The connector housing 344 defines at least one lumen 330 into which a proximal end 306 of the lead body 106' with terminals 310 can be inserted, as shown by directional arrow 338. The lead extension connector 322 also includes a plurality of connector contacts 340. When the lead body 106' is inserted into the lumen 330, the connector contacts 340 disposed in the connector housing 344 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector disposed in another lead extension. In other embodiments (as shown in FIG. 3C), the proximal end 348 of the lead extension 324 is configured and arranged for insertion into the connector 144 disposed on the control module 102'.

It will be understood that the control modules 102/102' can receive either lead bodies 106/106' or lead extensions 324. It will also be understood that the electrical stimulation system 100 can include a plurality of lead extensions 324. For example, each of the lead bodies 106 shown in FIGS. 1 and 3A can, alternatively, be coupled to a different lead extension 324 which, in turn, are each coupled to different ports of a two-port control module, such as the control module 102 of FIGS. 1 and 3A.

Figure 4:
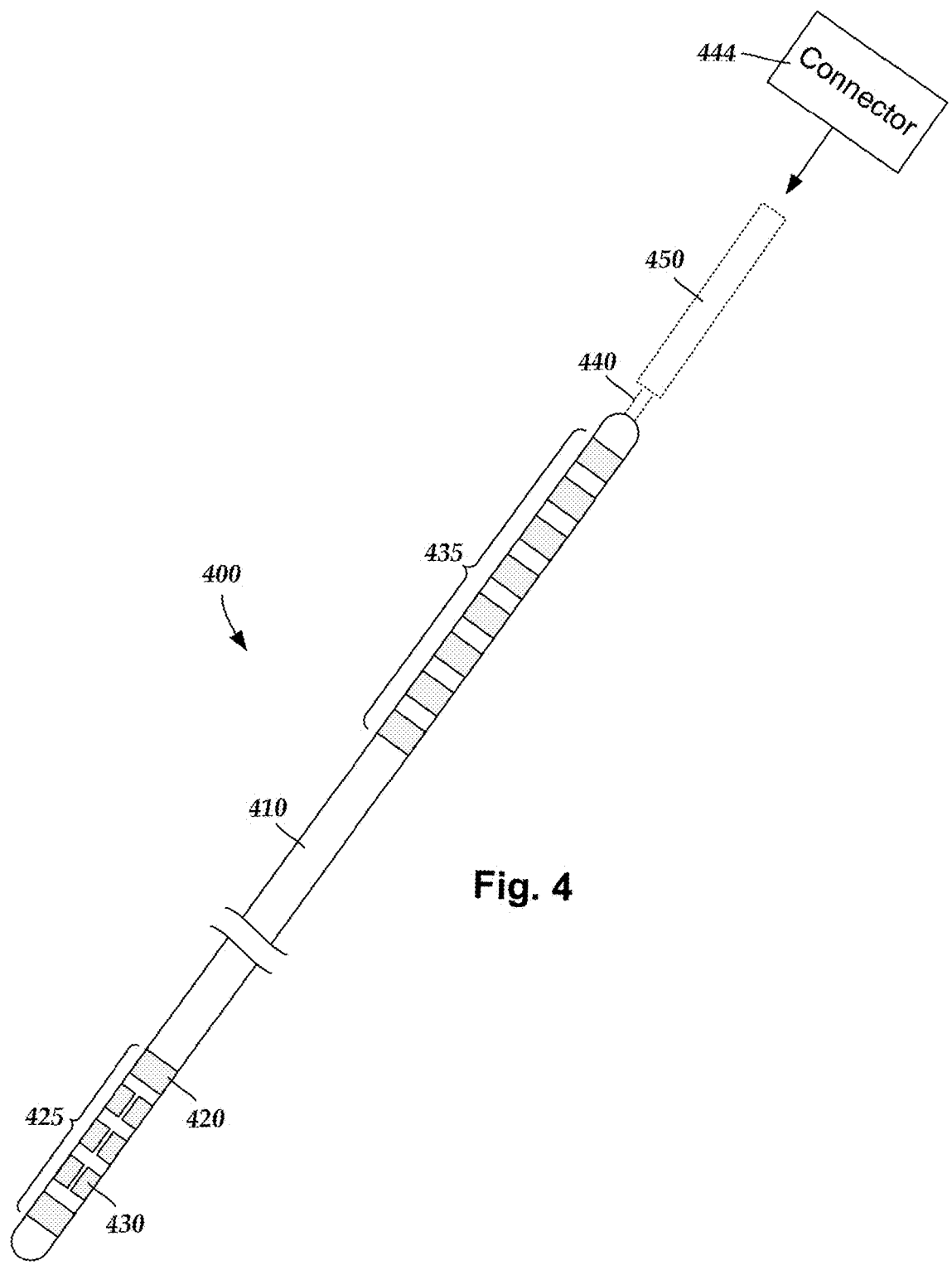
FIG. 4 is a schematic side view of yet another embodiment of an implantable medical device for brain stimulation, according to the invention.

Turning to FIG. 4, in the case of deep brain stimulation, the lead may include stimulation electrodes, recording electrodes, or a combination of both. At least some of the stimulation electrodes, recording electrodes, or both are provided in the form of segmented electrodes that extend only partially around the perimeter (for example, the circumference) of the lead. These segmented electrodes can be provided in sets of electrodes, with each set having electrodes circumferentially distributed about the lead at a particular longitudinal position.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

FIG. 4 illustrates one embodiment of a device 400 for brain stimulation. The device includes a lead 410, a plurality of electrodes 425 disposed at least partially about a perimeter of the lead 410, a plurality of terminals 435, a connector 444 for connection of the electrodes to a control unit, and a stylet 440 for assisting in insertion and positioning of the lead in the patient's brain. The stylet 440 can be made of a rigid material. Examples of suitable materials for the stylet include, but are not limited to, tungsten, stainless steel, and plastic. The stylet 440 may have a handle 450 to assist insertion into the lead 410, as well as rotation of the stylet 440 and lead 410. The connector 444 fits over a proximal end of the lead 410, preferably after removal of the stylet 440.

In FIG. 4, the electrodes 425 are shown as including both ring electrodes, such as ring electrode 420, and segmented electrodes, such as segmented electrodes 430. In some embodiments, the electrodes 425 are all segmented. In other embodiments, the electrodes 425 are all ring-shaped. In FIG. 4, each of the terminals 435 is shown as being ring-shaped. The segmented electrodes of FIG. 4 are shown in sets of two, where the two segmented electrodes of a particular set are electrically isolated from one another and are circumferentially offset along the lead 410. Any suitable number of segmented electrodes can be formed into a set including, for example, two, three, four, or more segmented electrodes.

Segmented electrodes can be used to direct stimulus current to one side, or even a portion of one side, of the lead. When segmented electrodes are used in conjunction with an implantable pulse generator that delivers current stimulus, current steering can be achieved to more precisely deliver the stimulus to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a perimeter of the lead. This provides precise three-dimensional targeting and delivery of the current stimulus to neural target tissue, while potentially avoiding stimulation of other tissue. Examples of leads with segmented electrodes include U.S. Pat. Nos. 6,295,944; and 6,391,985; and U.S. Patent Applications Publication Nos. 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated herein by reference in their entirety.

Figure 5A:
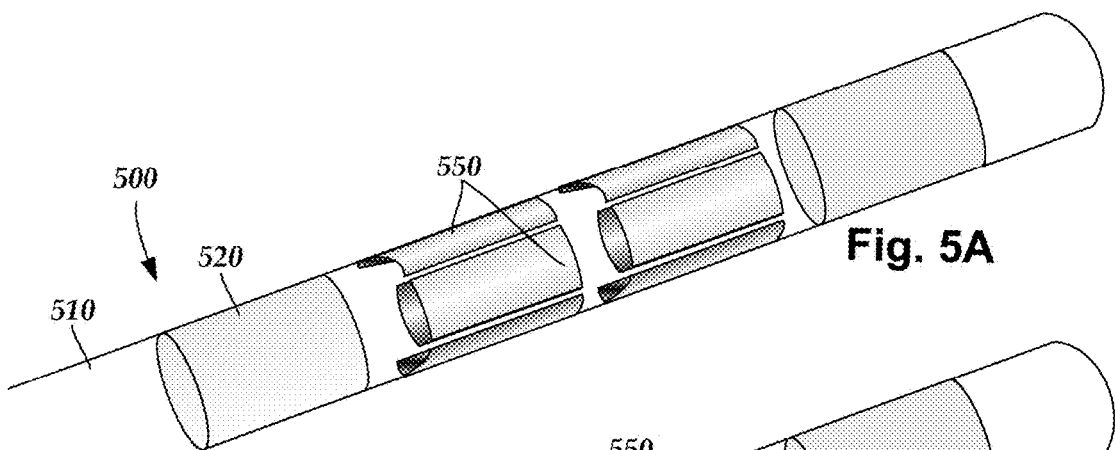
FIG. 5A is a schematic perspective view of one embodiment of a distal end of a lead containing segmented electrodes, according to the invention.
Figure 5B:
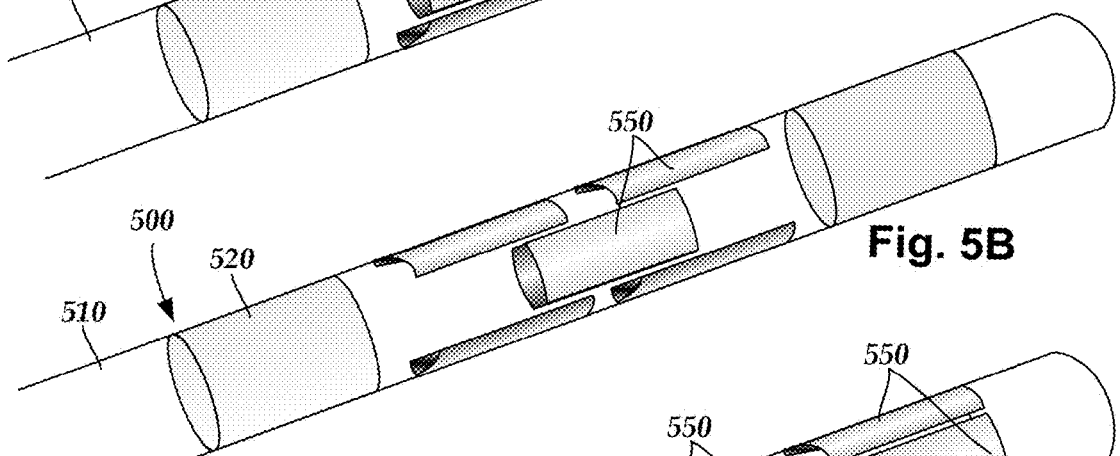
FIG. 5B is a schematic perspective view of a second embodiment of a distal end of a lead containing segmented electrodes, according to the invention.
Figure 5C:
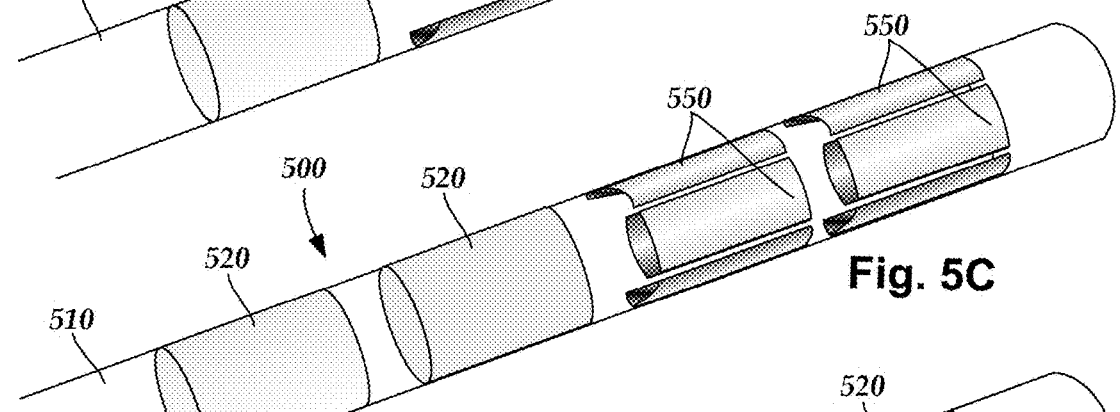
FIG. 5C is a schematic perspective view of a third embodiment of a distal end of a lead containing segmented electrodes, according to the invention.
Figure 5D:
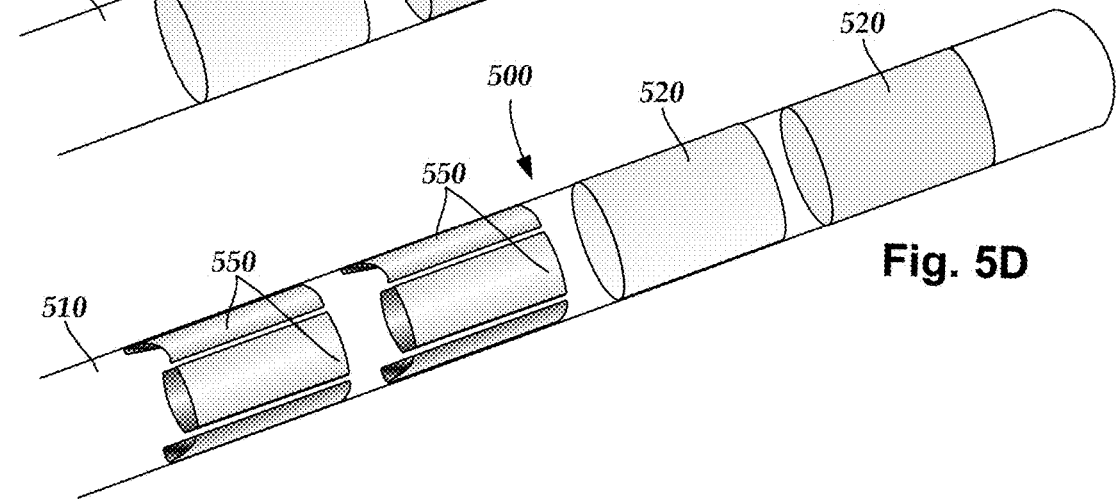
FIG. 5D is a schematic perspective view of a fourth embodiment of a distal end of a lead containing segmented electrodes, according to the invention.
Figure 5E:
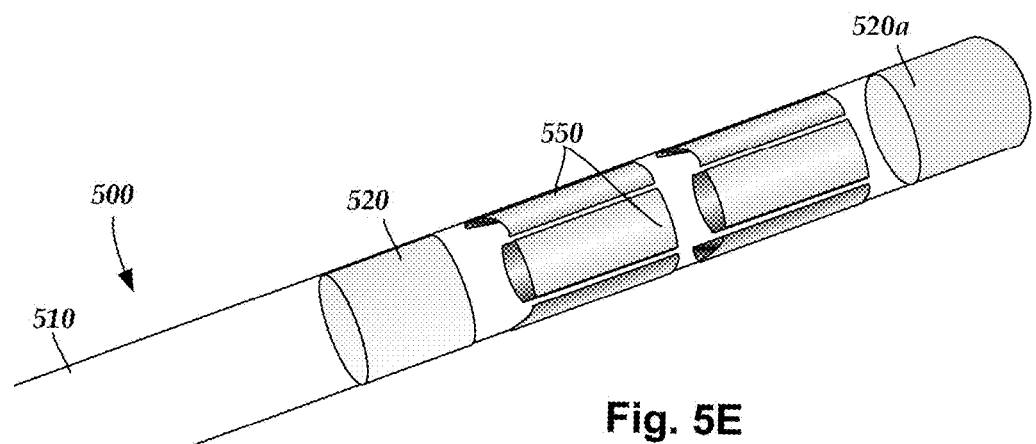
FIG. 5E is a schematic perspective view of a fifth embodiment of a distal end of a lead containing segmented electrodes, according to the invention.
Figure 5F:
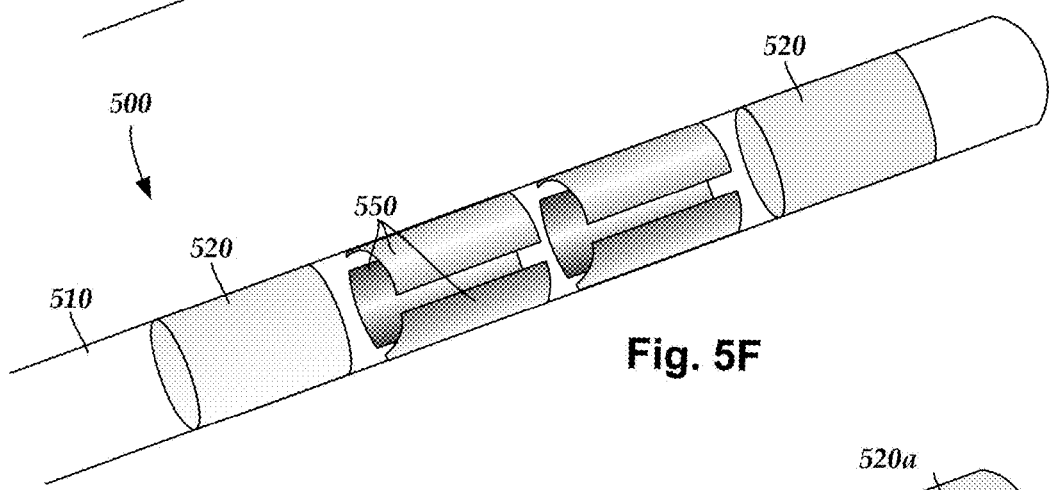
FIG. 5F is a schematic perspective view of a sixth embodiment of a distal end of a lead containing segmented electrodes, according to the invention.

FIGS. 5A-5H illustrate leads 500 with segmented electrodes 550, optional ring electrodes 520 or tip electrodes 520a, and a lead body 510. The sets of segmented electrodes 550 each include either two (FIG. 5B), three (FIGS. 5E-5H), or four (FIGS. 5A, 5C, and 5D) or any other number of segmented electrodes including, for example, three, five, six, or more. The sets of segmented electrodes 550 can be aligned with each other (FIGS. 5A-5G) or staggered (FIG. 5H).

When the lead 500 includes both ring electrodes 520 and segmented electrodes 550, the ring electrodes 520 and the segmented electrodes 550 may be arranged in any suitable configuration. For example, when the lead 500 includes two ring electrodes 520 and two sets of segmented electrodes 550, the ring electrodes 520 can flank the two sets of segmented electrodes 550 (see e.g., FIGS. 1, 5A, and 5E-5H). Alternately, the two sets of ring electrodes 520 can be disposed proximal to the two sets of segmented electrodes 550 (see e.g., FIG. 5C), or the two sets of ring electrodes 520 can be disposed distal to the two sets of segmented electrodes 550 (see e.g., FIG. 5D). One of the ring electrodes can be a tip electrode (see, tip electrode 520a of FIGS. 5E and 5G). It will be understood that other configurations are possible as well (e.g., alternating ring and segmented electrodes, or the like).

By varying the location of the segmented electrodes 550, different coverage of the target neurons may be selected. For example, the electrode arrangement of FIG. 5C may be useful if the physician anticipates that the neural target will be closer to a distal tip of the lead body 510, while the electrode arrangement of FIG. 5D may be useful if the physician anticipates that the neural target will be closer to a proximal end of the lead body 510.

Figure 5G:
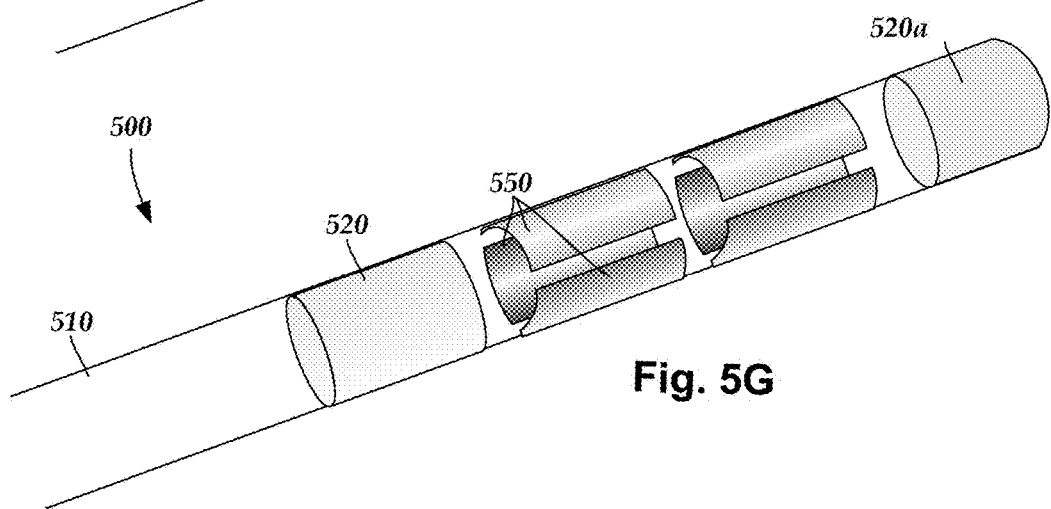
FIG. 5G is a schematic perspective view of a seventh embodiment of a distal end of a lead containing segmented electrodes, according to the invention.

Any combination of ring electrodes 520 and segmented electrodes 550 may be disposed on the lead 500. For example, the lead may include a first ring electrode 520, two sets of segmented electrodes; each set formed of four segmented electrodes 550, and a final ring electrode 520 at the end of the lead. This configuration may simply be referred to as a 1-4-4-1 configuration (FIGS. 5A and 5E—ring electrodes 520 and segmented electrode 550). It may be useful to refer to the electrodes with this shorthand notation. Thus, the embodiment of FIG. 5C may be referred to as a 1-1-4-4 configuration, while the embodiment of FIG. 5D may be referred to as a 4-4-1-1 configuration. The embodiments of FIGS. 5F, 5G, and 5H can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 550 are disposed on the lead. The 1-3-3-1 electrode configuration of FIGS. 5F, 5G, and 5H has two sets of segmented electrodes, each set containing three electrodes disposed around the perimeter of the lead, flanked by two ring electrodes (FIGS. 5F and 5H) or a ring electrode and a tip electrode (FIG. 5G). In some embodiments, the lead includes 16 electrodes. Possible configurations for a 16-electrode lead include, but are not limited to 4-4-4-4; 6-8; 5-3-3-3-3-1 (and all rearrangements of this configuration); and 2-2-2-2-2-2-2-2. Any other suitable segmented electrode arrangements (with or without ring electrodes) can be used including, but not limited to, those disclosed in U.S. Provisional Patent Application Ser. No. 62/113,291 and U.S. Patent Applications Publication Nos. 2012/0197375 and 2015/0045864, all of which are incorporated herein by reference in their entirety.

In at least some embodiments, a lead with 16 electrodes also includes 16 terminals. Many conventional control modules and connectors are designed to accept a proximal end of a lead or lead extension with an array of eight terminals. To instead have 16 terminals could extend the length of the proximal end of the lead or lead extension and a consequent increase in the size of connector or control module.

Instead, in at least some embodiments it may be advantageous to design an elongate member (e.g., a lead, lead extension, splitter, adaptor, or the like) with segmented terminals forming a split proximal contact array. In at least some embodiments, the elongate member also includes segmented electrodes. Utilizing a split proximal contact array may reduce the physical size of the terminal array when compared to conventional terminal arrays with ring-shaped terminals. Consequently, the portion of the elongate member that is inserted into a connector to make electrical contact with the pulse generator can be reduced, as compared to conventional electrical stimulation systems. Alternately, the number of terminals that can be disposed along a proximal portion of an elongate member and that can be inserted into a conventionally sized connector may be increased from conventional electrical stimulation systems. Some examples of such arrangements are found in, for example, U.S. Provisional Patent Application Ser. No. 62/113,291, incorporated herein by reference in its entirety.

Although the embodiments described below are presented as leads, it will be understood that the arrangement of segmented terminals, a retention sleeve, and an alignment slit, described below, can also be applied to a lead extension or other elongate member having terminals. In general, any elongate member can have first contacts (for example, electrode for a lead or conductive contacts for a lead extension) disposed along a distal portion of the elongate member and second segmented contacts (for example, segmented terminals) disposed along a proximal portion of the elongate member.

FIG. 6A illustrates one embodiment of a proximal portion of a lead 603 (or other elongate member) with a split proximal contact array of segmented terminals 610 and an optional retention sleeve 670. To ensure proper alignment between of the lead 603 (or other elongate member) in a connector 644 (FIGS. 7A-7D) so that each terminal is electrically connected to a single connector contact, the lead includes an alignment slit 682 formed along a portion of the proximal end of the lead. The alignment slit 682 extends completely through the lead 603 and intersects a central lumen 686 (or stylet lumen) of the lead, as shown in FIG. 6C. The alignment slit 682 separates the proximal portion of the lead into at least two sections 603a, 603b that are laterally spaced-apart and separated by the alignment slit.

The segmented terminals 610 can be formed in sets of two or more terminals at a same position along the longitudinal axis of the lead. Each of the segmented terminals of a particular set extends around less than (for example, no more than 45%, 40%, 33%, 30%, or 25% of) the entire perimeter of the elongate member. The segmented terminals of the set are not in electrical contact with one another and are circumferentially offset from one another along the elongate member. In at least some embodiments, the terminal array includes at least one segmented terminal set, such as segmented terminal set 611 which, in turn, includes multiple segmented terminals 610, such as segmented terminals 610a and 610b. In some embodiments, a set of segmented terminals can have two, three, four, or more segmented terminals disposed at the same position along the longitudinal axis of the elongate member, but circumferentially offset from each other. In at least some embodiments, the alignment slit 682 extends between at least two of the segmented terminals of one or more (or even each) of the sets of segmented terminals. In at least some of these embodiments, each set includes exactly two segmented terminals.

In some embodiments, the terminal array is formed exclusively from segmented terminals. In other embodiments, the terminal array includes a combination of one or more ring-shaped terminals and one or more segmented terminal sets.

The terminal array can include any suitable number of segmented terminal sets 611 including, for example, one, two, three, four, five, six, seven, eight, nine, ten eleven, twelve, thirteen, fourteen, fifteen, sixteen, or more segmented-terminal sets. In FIG. 6A, eight segmented terminal sets 611 are shown disposed along the lead 603.

In at least some embodiments, the elongate member includes a single proximal portion and multiple distal portions. One advantage of implementing segmented terminals is that it may increase the number of terminals disposed along a lead from conventional leads. The increased number of terminals may enable the lead to be designed with multiple distal portions, where a different electrode array is disposed along each of the distal portions, and where electrodes of each of the multiple electrode arrays are coupled to terminals disposed along a single proximal portion. Such a design may be useful, for example, in deep brain stimulation where bilateral stimulation may be desirable.

When the lead has multiple distal portions and a single proximal portion with segmented terminals, the single proximal portion can be received by a single connector port. Such an arrangement enables each of multiple electrode arrays disposed along different distal portions to be operated by a single control module. Additionally, such a design enables multiple electrode arrays to be controlled by a single control module via a single connector with a single lead-receiving port.

In FIG. 6A, the alignment slit 682 extends from the proximal end of the lead to a point beyond the retention sleeve 670. The alignment slit 682 separates the terminals 610a, 610b in each set 611 and divides the retention sleeve 670 into two parts that are laterally spaced-apart and separated from each other by the alignment slit. FIG. 6B illustrates an alternative embodiment of the lead 603 and the alignment slit 682 where the alignment slit 682 terminates distal to all of the terminals 610, but proximal to the retention sleeve 670. It will be understood that in other embodiments, the alignment slit can terminate anywhere along the array of terminals 610.

In the embodiment of FIG. 6D, the alignment slit 682 only extends partway into the lead 603 to the central lumen 686, as illustrated in FIG. 6E.

In FIGS. 6A, 6B, and 6D, the terminals 610 of each set are aligned with each other to form longitudinal columns (i.e., columns parallel to the longitudinal axis of the lead) of terminals that are aligned. In other embodiments, segmented terminals can be arranged in longitudinal columns with the columns being longitudinally offset from each other (for example, the terminals on the left could be longitudinally offset from those on the right). In some embodiments, the terminals of different longitudinal columns do not overlap and in other embodiments, the terminals of different longitudinal columns do overlap. It will be recognized that other arrangements of segmented terminals, including any of those arrangements described above with respect to arrangements of segmented terminals, can be used.

With respect to leads with the terminal arrays illustrated in FIGS. 6A, 6B, and 6D, the corresponding electrodes can be segmented electrodes, ring electrodes, other electrodes disclosed herein, or any other suitable electrode, or any combination thereof. In particular, although the terminals of a lead may be all or part segmented terminals, the corresponding electrodes may be segmented electrodes, non-segmented electrodes, or any combination thereof.

Turning to FIGS. 7A-7D, the proximal portion of the elongate member, such as the lead 603 (FIGS. 6A, 6B, and 6D), is typically inserted into a connector 644 disposed on or along a lead extension, control module, adaptor, splitter, or the like. The connector 644 includes segmented connector contacts 640 suitable for coupling with the segmented terminals. The connector 644 includes an elongated connector housing 660 that defines a connector lumen 662 suitable for receiving a portion of an elongate member, such as the lead 603 (FIGS. 6A, 6B, and 6D); a lead extension (e.g., 324 in FIG. 3C); or the like. Although the illustrated connector lumen has a circular cross-section, it will be understood that lumens with other cross-sections (and leads with non-circular cross-sections) can also be used including, but not limited to, oval, square, rectangular, triangular, pentagonal, hexagonal, octagonal, cruciform, or any other suitable regular or irregular cross-sectional shape.

The connector 644 also includes an alignment structure 680 (for example, a pin, blade, seal, wall, rod, or rail) that extends into the connector lumen 662 and can be used to align the lead with the connector by mating with the alignment slit 682 of the lead. The embodiment of FIG. 7A illustrates the alignment structure 680 extending across the entire diameter of the connector lumen 662 and can be used with, for example, the leads of FIGS. 6A and 6B. The embodiment of FIG. 7B illustrates the alignment structure 680 extending only partway (for example, 30%, 40%, 50%, or 60% or less) across the diameter of the connector lumen 662 and can be used with, for example, the lead of FIG. 6D (or even the leads of FIGS. 6A and 6B).

Multiple connector contacts 640 are disposed in a spaced-apart relationship along the longitudinal length of the connector housing 660 such that the connector contacts are exposed to the connector lumen 662 (FIGS. 7A and 7B) and individually attached to an array of conductive members (for example, wires, pins, traces, terminals, or the like) that couple the connector contacts to other components. When, for example, the connector 644 is disposed on a lead extension (e.g., 324 in FIG. 3C), the conductive members (for example, wires or other conductors) may couple the connector contacts to lead extension terminals. When, for example, the connector 644 is disposed on a control module, the conductive members (for example, wires, traces, pins, or the like) may couple the connector contacts 640 to the electronic subassembly (110 in FIG. 1). In at least some embodiments, the conductive members 664 couple the connector contacts 640 to the electronic subassembly (110 in FIG. 1) via feedthrough pins extending through the sealed housing (114 in FIG. 1).

In at least some embodiments, the segmented connector contacts 640 can be formed in sets of two or more terminals at a same position along the longitudinal axis of the connector lumen 662. Each of the segmented connector contacts of a particular set extends around less than (for example, no more than 45%, 40%, 33%, 30%, 25%, 20%, 15%, or 10% of) the entire perimeter of the connector lumen. The segmented connector contacts of the set are not in electrical contact with one another and are circumferentially offset from one another along the connector lumen. In at least some embodiments, the connector contact array includes at least one segmented connector contacts set, such as segmented connector contacts set 641 which, in turn, includes multiple segmented connector contacts 640, such as segmented terminals 640a and 640b. In some embodiments, a set of segmented connector contacts can have two, three, four, or more segmented connector contacts disposed at the same position along the longitudinal axis of the connector lumen, but circumferentially offset from each other.

Optionally, a retention block 666 is disposed along the connector 644. The retention block 666 can be used to facilitate retention of an elongate member when the elongate member is inserted into the connector lumen 662. In at least some embodiments, the retention block 666 defines a fastening aperture 668 configured to receive a fastener (e.g., a set screw, pin, or the like) which can engage the optional retention sleeve 670 (FIG. 6A) of the lead. In at least some embodiments, the fastener, when received by the fastener aperture 668, is configured to tighten against a portion of the elongate member (e.g., a retention sleeve) when the elongate member is inserted into the connector lumen 662.

The connector 644 includes an alignment structure 680 that mates with or fits within the alignment slit 682 of the lead 603. Engagement of the alignment structure 680 of the connector 644 with the alignment slit 682 of the lead 603 ensures that the lead and connector have the proper rotational alignment for correctly coupling the segmented terminals 610 of the lead 603 with the connector contacts 640 of the connector 644.

In the embodiment of FIG. 7C, the alignment structure 680 is disposed in the proximal end of the retention block 666. This particular arrangement is useful with the leads 603 of FIGS. 6A and 6D where the alignment slit 670 extends through the retention sleeve 670. The alignment structure 680 can be placed elsewhere in the connector 644. For example, in the embodiment illustrated in FIG. 7D, the alignment structure 680 is placed at the distal end of the retention block 666. This arrangement can be used with any of the lead illustrated in FIG. 6B (and also the leads of FIGS. 6A and 6D). In other embodiments, the alignment structure 680 can be placed outside the retention block. In at least some embodiments, the alignment structure can extend between one or more (or even all) of the connector contacts 640. In yet other embodiments, the alignment structure 680 can be placed in other portions of the connector lumen 662, such as near the end of the connector lumen.

When using a split proximal contact array, the corresponding connector on a lead extension or within a control module, splitter, operating room cable, or the like also includes a split array of contacts within the connector. A variety of different contact arrays can be used.

FIGS. 8A-8E illustrate one embodiment of a connector 844 for receiving a split proximal contact array. FIG. 8A illustrates one embodiment of a carrier 850 that fits within the connector 844 (FIGS. 8D and 8E). The carrier 850 includes a body 851 having opposing rails 852, opposing contact holders 853 spaced-apart along the rails, openings 854 between pairs of contact holders, an optional retainer element 855 with an opening 856, and an optional stop element 857. A pair of opposing contact holders 853a, 853b is illustrate in FIG. 8A with each of the contact holders coupled to a different one of the rails 852. In addition, optionally, a pair of opposing contact holders can be integrated with one of, or each of, the optional retainer element 855 and the optional stop element 857, as illustrated in FIG. 8A.

The carrier 850 can be formed of any non-conductive material including, for example, a plastic material such as silicone, polyurethane, polyetheretherketone, or the like. In at least some embodiments, the non-conductive material is a plastic material that is more rigid than the plastic material used in a lead body. The carrier 850 can be formed as a single piece or as multiple pieces that are joined together. The opening 856 in the optional retainer element 855 can be sized to receive a fastener, such as a screw or rod that can engage a lead inserted into the connector 844 to hold the lead within the connector. The optional stop element 857 can be arranged to resist further insertion of the lead into a connector 844 and, thereby, facilitate proper alignment of the terminals of the lead with the contacts 840 (FIG. 8B) of the connector.

FIG. 8B illustrates one embodiment of a contact 840 that can be disposed between two of the opposing contact holders 853 (see, FIGS. 8D and 8E). Two contacts 840 are disposed between each pair of opposing contact holders 853a, 853b (FIG. 8A) of the carrier 850. These two contacts 840 are typically not in electrical contact with each other, but are separated by, for example, the rails 852 and the connector lumen 662. In at least some embodiments, the contacts 840 are fit into the contact holders 853 so that the contacts can shift slightly backwards when a lead is inserted into the connector lumen and passes the contact. This shifting can create a contact point between the contact and a terminal on the lead.

Each contact 840 is formed of a conductive material, including any of the material described above for use in making electrodes or terminals. Each contact 840 is coupled to a conductor (not shown), such as a wire that extends from the connector 844 along an extension body if the connector is part of a lead extension or to a wire or feedthrough if the connector 844 is part of a control module. In some embodiments, the contact 840 can be stamped from a metal sheet and folded or otherwise formed into the shape illustrated in FIG. 8B. In the illustrated embodiment, the contact 840 includes an opening 840a along one edge and an open interior 840b.

FIG. 8C illustrates one embodiment of a non-conductive spacer 858. The spacer 858 is arranged to fit within the opening 854 between longitudinally adjacent contact holder 853 to space apart and electrically isolate contacts 840 that are longitudinally adjacent to each other. The spacer 858 can include an opening 858a which receives one of the rails 852. In some embodiments, the spacer 858 can include an indent opposite the opening 858a to receive the other rails 852. The spacers 858 can be made of any suitable non-conductive material including, but not limited to, silicone, polyurethane, polyetheretherketone (PEEK), or the like.

FIGS. 8D and 8E illustrate the connector 844 with an extension body 845 extending from the connector 844. The connector 844 includes a connector body 860 and an entrance snout 859. The connector body 860 fits around the carrier 850, contacts 840, and spacers 858 and can optionally include an opening corresponding to the opening 856 in the optional retainer element 855 of the carrier 850 so that a fastener can be inserted, as described above. The connector body 860 can be made of any biocompatible, non-conductive material such as, for example, silicone, polyurethane, polyetheretherketone (PEEK), or the like. In at least some embodiments, the connector body 860 is made of a material that is less rigid than the material used to form the carrier 850 so that the connector body 860 provides a flexible or compressible surface that is less damaging to tissue than the carrier.

The entrance snout 859 has an opening to receive the lead and may have ridged features 861 on the interior surface to reduce or prevent tissue entry into the connector 844. Moreover, the ridged features 861 may also form a seal with the lead to reduce or prevent fluid entry into the connector 844. The entrance snout 859 may be tapered, as illustrated in FIG. 8D. The entrance snout can also be incorporated in any of the other connectors described herein.

Figure 9A:
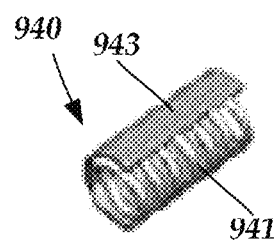
FIG. 9A is a schematic perspective view of one embodiment of a contact for a connector, according to the invention.
Figure 9B:
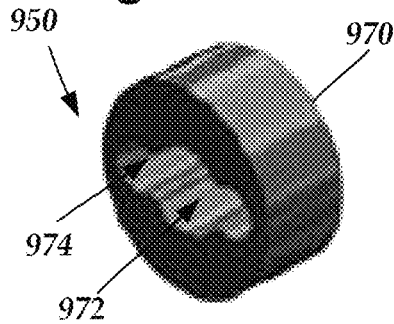
FIG. 9B is a schematic perspective view of one embodiment of a contact carrier for a connector, according to the invention.

FIGS. 9A-9D illustrate one embodiment of a connector 944 for receiving a split proximal contact array. FIG. 9A illustrates one embodiment of a contact 940 and FIG. 9B illustrates one embodiment of a contact carrier 950. Two contacts 940 are disposed opposite one another in each contact carrier 950. These two contacts 940 are typically not in electrical contact with each other, but are separated by the contact carrier 950 and the connector lumen 662.

Each contact 940 is formed of a coil 941 disposed in a curved conductive sheath 943, as illustrated in FIG. 9A. The coil 941 and sheath 943 can be formed of any conductive material, including any of the material described above for use in making electrodes or terminals. Each sheath 943 is coupled to a conductor (not shown), such as a wire that extends from the connector 944 along an extension body if the connector is part of a lead extension or to a wire or feedthrough if the connector 944 is part of a control module.

The coil 941 can be, for example, a spring or other resilient construct. The sheath 943 can extend around the entire circumference of the sheath or only around a portion (for example, at least 80%, 75%, 67%, or 50%) of the circumference of the sheath, as illustrated in FIG. 9A. The coil 941 can compress against the sheath 943 when the lead is inserted into the connector 944 and provide a contact point with a terminal on the lead.

FIG. 9B illustrates one embodiment of the non-conductive contact carrier 950. The contact carrier 950 has a body 970 and a lumen 972 that includes two nodes 874 designed to each receive one of the two contacts 940. The contact carrier 950 can be made of any suitable non-conductive material including, but not limited to, silicone, polyurethane, polyetheretherketone (PEEK), or the like. In at least some embodiments, the contacts 940 can fit in the contact carrier 950 in the longitudinal orientation (i.e., with the longitudinal axis of the coil 941 parallel to the longitudinal axis of the connector 944), as illustrated in FIGS. 9A-9D. In other embodiments, the contacts 940 and contact carrier can be arranged so that the contacts are disposed vertically with the longitudinal axis of the coil perpendicular to the longitudinal axis of the connector (similar to the arrangement described below with respect to FIGS. 10A-10E). In yet other embodiments, the longitudinal axis of the coil of the contact may be at an angle between 0 to 90 degrees (i.e., not parallel or perpendicular) with respect to the longitudinal axis of the connector. In these other embodiments, the lumen of the contact carrier would be different from that illustrated in FIG. 9B to accommodate the alternative arrangement of the contacts within the contact carrier.

Figure 9C:
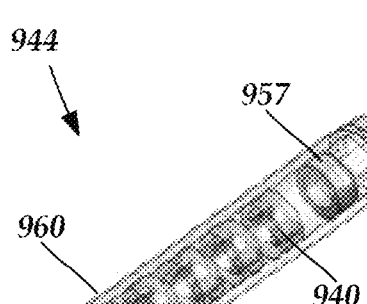
FIG. 9C is a schematic perspective view of one embodiment of a connector incorporating the elements of FIGS. 9A-9B, according to the invention.
Figure 9D:
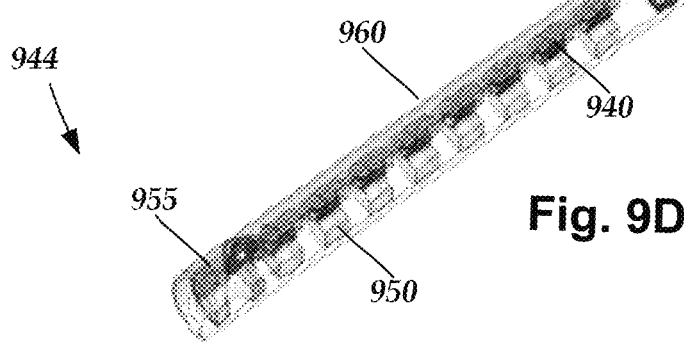
FIG. 9D is a schematic perspective cut-away view of the connector of FIG. 9C, according to the invention.

FIGS. 9C and 9D illustrate the connector 944 with an extension body 945 extending from the connector 944. The connector 944 includes a connector body 960, an optional retainer element 955, and an optional end stop element 957. The connector body 960 and the optional retainer element 955 can include an opening 956 through which a fastener (such as a screw, rod, or the like) can be inserted to contact and hold a lead disposed within the connector 944. The connector body 960 fits around the contact carriers 950 and contacts 940. The connector body 960 can be made of any biocompatible, non-conductive material such as, for example, silicone, polyurethane, polyetheretherketone (PEEK), or the like.

In at least some embodiments, the contacts 940 are disposed in the contact carriers 950 which are then disposed in a mold with the optional retainer element 955 and optional end stop element 957. The connector body 960 is formed by molding around the contact carriers 950, optional retainer element 955, and optional end stop element. A mandrel or other element can be positioned in the mold to form the connector lumen.

Figure 10A:
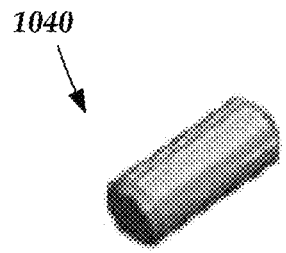
FIG. 10A is a schematic perspective view of one embodiment of a contact for a connector, according to the invention.
Figure 10C:
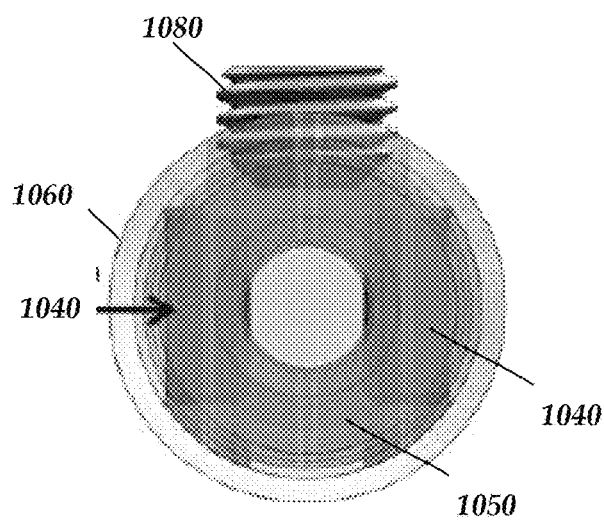
FIG. 10C is a schematic end view of one embodiment of a connector with portions of the connector made translucent for purposes of illustrating an arrangement of the contacts, according to the invention.
Figure 10B:
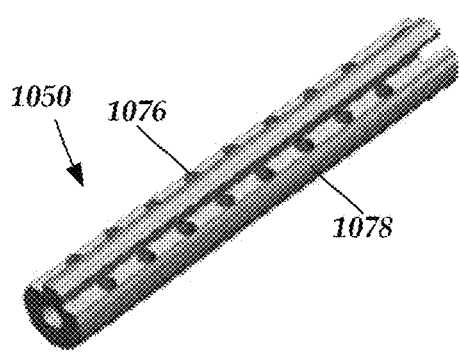
FIG. 10B is a schematic perspective view of one embodiment of a contact carrier for a connector, according to the invention.

FIGS. 10A-10E illustrate one embodiment of a connector 1044 for receiving a split proximal contact array. FIG. 10A illustrates one embodiment of a contact 1040 and FIG. 10B illustrates one embodiment of a contact carrier 1050. Each contact 1040 is a rod or spring that can be formed of any conductive material, including any of the material described above for use in making electrodes or terminals. Each contact 1040 is coupled to a conductor (not shown), such as a wire that extends from the connector 1044 along an extension body if the connector is part of a lead extension or to a wire or feedthrough if the connector 1044 is part of a control module.

FIG. 10B illustrates one embodiment of the non-conductive contact carrier 1050. The contact carrier 1050 has a body 1078 and multiple openings 1076 designed to receive the contacts 1040. The openings 1076 can be arranged in pairs, as illustrated in FIG. 10B, so that two contacts 1040 are disposed opposite each other, as illustrated in FIG. 10C. Other arrangements of openings and contacts can also be used including, for example, an arrangement where the openings on one side are offset from the openings on the other side of the contact carrier. The contact carrier 1050 can be made of any suitable non-conductive material including, but not limited to, silicone, polyurethane, polyetheretherketone (PEEK), or the like. In at least some embodiments, the contact carrier is formed of a material that can act as a spring so that when a lead or lead extension is inserted into the connector, the lead or lead extension pushes against the contacts and the contact carrier is compressed.

In at least some embodiments, the contacts 1040 can fit in the contact carrier 1050 in perpendicular to the longitudinal axis of the connector 1044, as illustrated in FIGS. 10A-10E. In other embodiments, the contacts 1040 and contact carrier can be arranged so that the contacts are disposed vertically with the longitudinal axis of the coil perpendicular to the longitudinal axis of the connector (similar to the arrangement described below with respect to FIGS. 10A-10E). In yet other embodiments, the longitudinal axis of the coil of the contact may be at an angle between 0 to 90 degrees with respect to the longitudinal axis of the connector. In these other embodiments, the openings of the contact carrier would be arranged to accommodate this angle of the contacts.

Figure 10D:
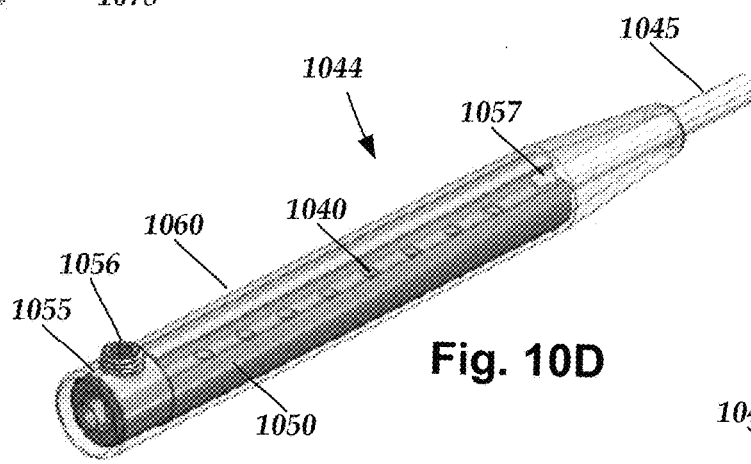
FIG. 10D is a schematic perspective view of one embodiment of a connector incorporating the elements of FIGS. 10A and 10B, according to the invention.
Figure 10E:
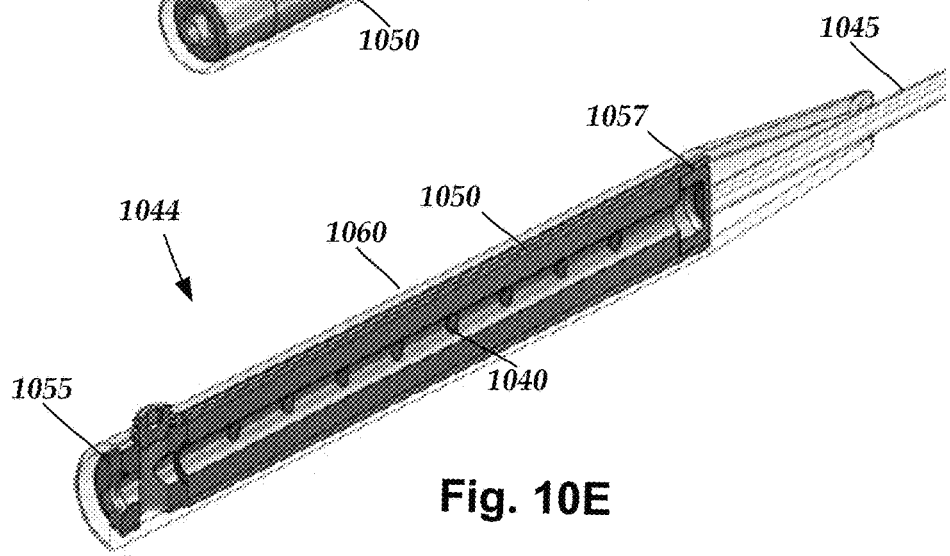
FIG. 10E is a schematic perspective cut-away view of the connector of FIG. 10D, according to the invention.

FIGS. 10C to 10E illustrate the connector 1044 with an extension body 1045 extending from the connector 1044. The connector 1044 includes a connector body 1060, an optional retainer element 1055, and an optional end stop element 1057. The connector body 1060 and the optional retainer element 1055 can include an opening 1056 through which a fastener 1080 (FIG. 10C) (such as a screw, rod, or the like) can be inserted to contact and hold a lead disposed within the connector 1044. The connector body 1060 fits around the contact carriers 1050 and contacts 1040. The connector body 1060 can be made of any biocompatible, non-conductive material such as, for example, silicone, polyurethane, polyetheretherketone (PEEK), or the like.

In at least some embodiments, the contacts 1040 are disposed in the contact carrier 1050 which is then disposed in a mold with the optional retainer element 1055 and optional end stop element 1057. The connector body 1060 is formed by molding around the contact carriers 1050, optional retainer element 1055, and optional end stop element. A mandrel or other element can be positioned in the mold to form the connector lumen.

Figure 11:
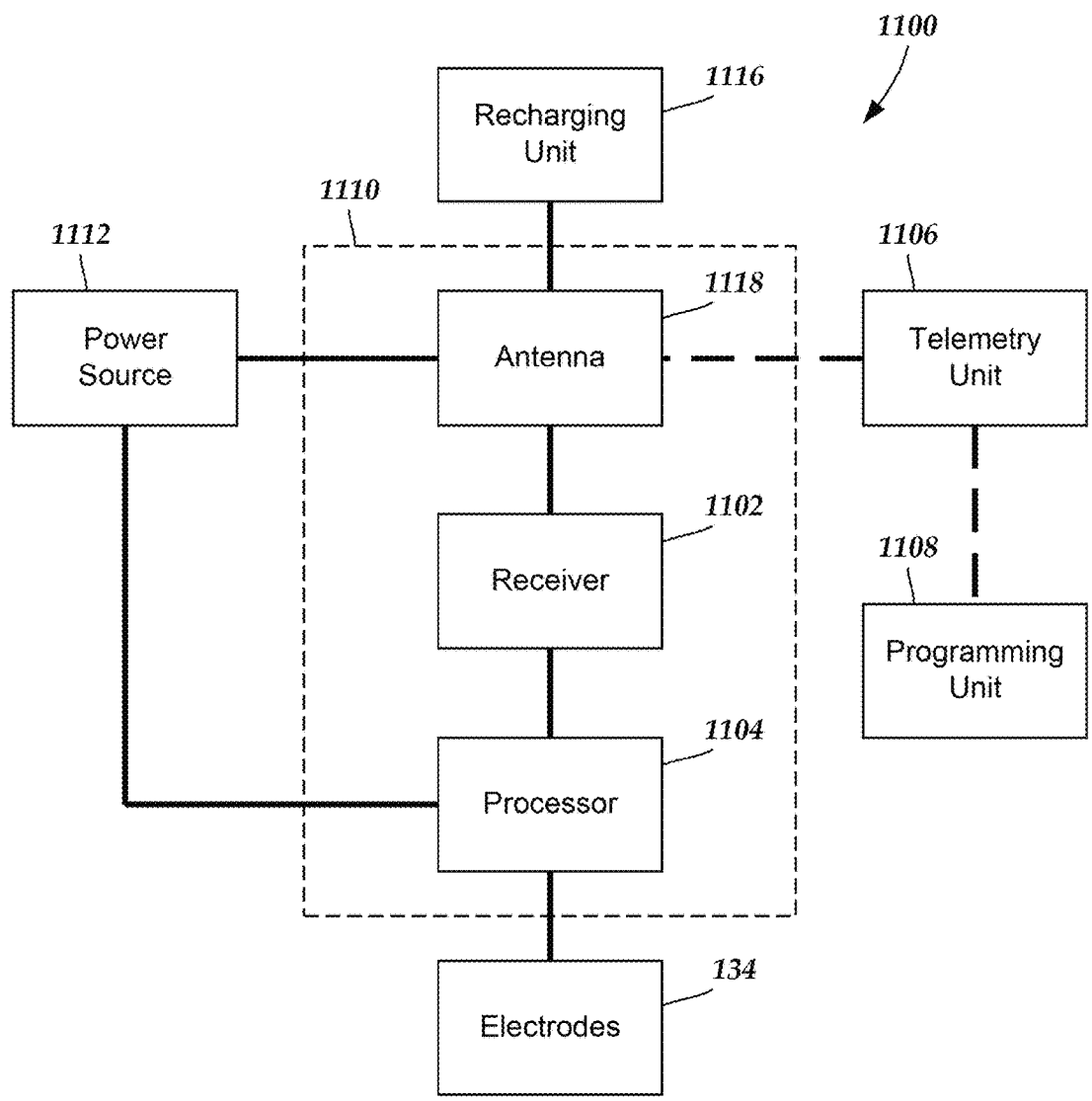
FIG. 11 is a schematic overview of one embodiment of components of an electrical stimulation system, according to the invention.

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, power source 1112, antenna 1118, receiver 1102, and processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 may select which electrode(s) are cathodes and which electrode(s) are anodes. In some embodiments, the processor 1104 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include an antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A connector for an implantable electrical medical device, the connector comprising:
    an elongated connector body having a first end and an opposing second end;
    a connector lumen defined in the connector body, the connector lumen configured and arranged to receive a lead or lead extension;
    a plurality of contact assemblies disposed in the connector lumen, each contact assembly comprising
        a non-conductive contact carrier defining a lumen with two nodes, and
        two contacts, each contact disposed in one of the two nodes such that the two contacts are not in electrical contact with one another, each contact comprising a coil; and
    a plurality of connector conductors electrically coupled to the plurality of contact assemblies.

2. The connector of claim 1, wherein a longitudinal axis of the coil of each contact is parallel to the connector lumen.

3. The connector of claim 1, wherein each contact further comprises a sheath disposed around at least a portion of the coil.

4. The connector of claim 3, wherein the sheath extends around at least 50% of a circumference of the coil.

5. The connector of claim 3, wherein the connector conductors are attached to the sheaths of the contacts of the contact assemblies.

6. The connector of claim 1, wherein the two nodes of each contact carrier are disposed opposite each other.

7. The connector of claim 1, wherein the two nodes of all of the contact carriers are aligned along the connector lumen.

8. The connector of claim 1, wherein a longitudinal axis of the coil of each contact is perpendicular to a longitudinal axis of the connector lumen.

9. The connector of claim 1, wherein a longitudinal axis of the coil of each contact is at an angle between, but not including, 0 and 90 degrees to a longitudinal axis of the connector lumen.

10. A lead extension comprising:
    a lead extension body with a proximal portion, a distal portion, a circumference, and a longitudinal length;
    the connector of claim 1 disposed along the distal portion of the lead extension body; and
    a plurality of lead extension terminals disposed along the proximal portion of the lead extension body;
    wherein the connector conductors electrically couple the contacts of the connector to the lead extension terminals.

11. A control module comprising:
    a sealed housing;
    an electronic subassembly disposed in the sealed housing;
    a header coupled to the sealed housing; and
    the connector of claim 1 disposed in the header.

12. A connector for an implantable electrical medical device, the connector comprising:
    an elongated connector body having a first end and an opposing second end;
    a connector lumen defined in the connector body, the connector lumen configured and arranged to receive a lead or lead extension;
    a non-conductive carrier disposed in the connector body and comprising a plurality of contact openings spaced apart from each other;
    a plurality of contacts, wherein each contact is a rod or spring disposed in one of the contact openings of the carrier; and
    a plurality of connector conductors coupled to the plurality of contacts.

13. The connector of claim 12, wherein the contacts are aligned perpendicular the connector lumen.

14. The connector of claim 12, wherein the plurality of contact openings form pairs of contact openings disposed opposite each other with respect to the connector lumen.

15. The connector of claim 12, wherein the plurality of contact openings forms two rows of contact openings with one of the rows of contact openings offset from another of the rows of contact openings.

16. The connector of claim 12, wherein the carrier is formed of a springy material that is compressed by the contacts when the lead or lead extension is received in the connector lumen.

17. The connector of claim 12, wherein a longitudinal axis of each contact is at an angle between, but not including, 0 and 90 degrees to a longitudinal axis of the connector lumen.

18. The connector of claim 12, wherein the carrier is a single piece of non-conductive material.

19. A lead extension comprising:
    a lead extension body with a proximal portion, a distal portion, a circumference, and a longitudinal length;
    the connector of claim 12 disposed along the distal portion of the lead extension body; and
    a plurality of lead extension terminals disposed along the proximal portion of the lead extension body;
    wherein the connector conductors electrically couple the contacts of the connector to the lead extension terminals.

20. A control module comprising:
    a sealed housing;
    an electronic subassembly disposed in the sealed housing;
    a header coupled to the sealed housing; and
    the connector of claim 12 disposed in the header.

* * * * *